(12) United States Patent
Gysling

(10) Patent No.: US 7,657,392 B2
(45) Date of Patent: Feb. 2, 2010

(54) METHOD AND APPARATUS FOR DETECTING AND CHARACTERIZING PARTICLES IN A MULTIPHASE FLUID

(75) Inventor: Daniel L. Gysling, Glastonbury, CT (US)

(73) Assignee: Cidra Corporate Services, Inc., Wallingford, CT (US)

( * ) Notice: Subject to any disclaimer, the term of this patent is extended or adjusted under 35 U.S.C. 154(b) by 0 days.

(21) Appl. No.: 11/435,675

(22) Filed: May 16, 2006

(65) Prior Publication Data
US 2007/0005272 A1    Jan. 4, 2007

Related U.S. Application Data

(60) Provisional application No. 60/681,925, filed on May 16, 2005.

(51) Int. Cl.
*G06F 15/00* (2006.01)
*G01N 31/00* (2006.01)

(52) U.S. Cl. ............... 702/128; 73/61.71; 73/736; 73/861.03; 73/861.44; 702/25; 702/45; 702/50; 702/137

(58) Field of Classification Search ............... 702/128, 702/33, 45–55, 137, 25; 324/300, 306; 73/53.01, 73/53.04, 61.42, 61.43, 61.44, 736, 61.48, 73/61.71, 861.03, 861.44
See application file for complete search history.

(56) References Cited

U.S. PATENT DOCUMENTS 3,751,979 A    8/1973    Ims
3,781,895 A    12/1973   Monser
3,851,521 A    12/1974   Ottenstein
3,885,432 A    5/1975    Herzl
3,952,578 A    4/1976    Jacobs
4,048,853 A    9/1977    Smith et al.
4,080,837 A    3/1978    Alexander et al.
4,248,085 A    2/1981    Coulthard
4,320,659 A    3/1982    Lynnworth et al.
4,445,389 A    5/1984    Potzick et al.

(Continued)

FOREIGN PATENT DOCUMENTS

DE    4306119    9/1994

(Continued)

OTHER PUBLICATIONS

Heywood, NI and D C-H Cheng, "Flow in Pipes Part2: Multiphase Flow" Phys. Technol. vol. 15 1984 pp. 291-300 and 314.

(Continued)

*Primary Examiner*—John H Le

(57) ABSTRACT

A method and apparatus for measuring the size and distribution of particles within a multiphase fluid flowing within a pipe is provided, wherein the apparatus includes at least one metering device for determining at least one of the mixture density of the fluid, the flow rate of the fluid and the dispersion of the fluid, wherein the at least one metering device generates meter data responsive to at least one of the mixture density of the fluid, the flow rate of the fluid and the dispersion of the fluid and a processing device communicated with the at least one metering device, wherein the processing device receives and processes the meter data to generate fluid information responsive to the size and distribution of the particles within the fluid.

28 Claims, 25 Drawing Sheets

U.S. PATENT DOCUMENTS

| | | | |
|---|---|---|---|
| 4,520,320 A | 5/1985 | Potzick et al. | |
| 4,539,649 A * | 9/1985 | Michaelis et al. | 702/137 |
| 4,561,310 A | 12/1985 | Barnard et al. | |
| 4,677,305 A | 6/1987 | Ellinger | |
| 4,717,159 A | 1/1988 | Alston et al. | |
| 4,896,540 A | 1/1990 | Shakkottai et al. | |
| 4,932,262 A | 6/1990 | Wlodarczyk | |
| 5,040,415 A | 8/1991 | Barkhoudarian | |
| 5,083,452 A | 1/1992 | Hope | |
| 5,218,197 A | 6/1993 | Carroll | |
| 5,285,675 A | 2/1994 | Colgate et al. | |
| 5,289,726 A | 3/1994 | Miau et al. | |
| 5,359,897 A | 11/1994 | Hamstead et al. | |
| 5,363,342 A | 11/1994 | Layton et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,591,922 A | 1/1997 | Segeral et al. | |
| 5,708,211 A | 1/1998 | Jepson et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,948,959 A | 9/1999 | Peloquin | |
| 6,016,702 A | 1/2000 | Maron | |
| 6,138,512 A | 10/2000 | Roberts et al. | |
| 6,151,958 A | 11/2000 | Letton et al. | |
| 6,202,494 B1 | 3/2001 | Riebel et al. | |
| 6,233,374 B1 | 5/2001 | Ogle et al. | |
| 6,349,599 B1 | 2/2002 | Lynnworth et al. | |
| 6,354,147 B1 | 3/2002 | Gysling et al. | |
| 6,378,357 B1 | 4/2002 | Han et al. | |
| 6,412,353 B1 | 7/2002 | Kleven et al. | |
| 6,435,030 B1 | 8/2002 | Gysling et al. | |
| 6,442,996 B1 | 9/2002 | Thurston et al. | |
| 6,443,226 B1 | 9/2002 | Diener et al. | |
| 6,449,563 B1 | 9/2002 | Dukhin et al. | |
| 6,450,037 B1 | 9/2002 | McGuinn et al. | |
| 6,463,813 B1 | 10/2002 | Gysling | |
| 6,536,291 B1 | 3/2003 | Gysling et al. | |
| 6,550,342 B2 | 4/2003 | Croteau et al. | |
| 6,558,036 B2 | 5/2003 | Gysling et al. | |
| 6,587,798 B2 | 7/2003 | Kersey et al. | |
| 6,601,005 B1 | 7/2003 | Eryurek | |
| 6,601,458 B1 | 8/2003 | Gysling et al. | |
| 6,609,069 B2 | 8/2003 | Gyslingj et al. | |
| 6,658,945 B1 | 12/2003 | Kleven | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,837,332 B1 | 1/2005 | Rodney | |
| 6,862,920 B2 | 3/2005 | Gysling et al. | |
| 6,889,562 B2 | 5/2005 | Gysling et al. | |
| 6,898,541 B2 | 5/2005 | Gysling et al. | |
| 6,959,604 B2 | 11/2005 | Davis et al. | |
| 7,146,864 B2 * | 12/2006 | Sullivan et al. | 73/861.42 |
| 7,152,003 B2 * | 12/2006 | Loose et al. | 702/45 |
| 7,171,315 B2 * | 1/2007 | Loose | 702/45 |
| 7,181,955 B2 | 2/2007 | Gysling | |
| 7,359,803 B2 * | 4/2008 | Gysling et al. | 702/25 |
| 7,379,828 B2 * | 5/2008 | Loose et al. | 702/50 |
| 2001/0020603 A1 | 9/2001 | Moorehead et al. | |
| 2002/0064331 A1 | 5/2002 | Gysling et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling | |
| 2003/0154036 A1 | 8/2003 | Gysling et al. | |
| 2003/0217605 A1 * | 11/2003 | Croteau et al. | 73/861.44 |
| 2004/0006409 A1 | 1/2004 | Liljenberg et al. | |
| 2004/0016284 A1 | 1/2004 | Gysling | |
| 2004/0069069 A1 * | 4/2004 | Gysling et al. | 73/736 |
| 2004/0074312 A1 | 4/2004 | Gysling | |
| 2004/0112122 A1 * | 6/2004 | Steward | 73/61.71 |
| 2005/0034532 A1 * | 2/2005 | Wible | 73/861.03 |
| 2005/0246111 A1 * | 11/2005 | Gysling et al. | 702/45 |

FOREIGN PATENT DOCUMENTS

| | | |
|---|---|---|
| EP | 0290336 | 11/1988 |
| GB | 2210169 | 6/1989 |
| WO | WO 9314382 | 7/1993 |
| WO | WO 0000793 | 1/2000 |
| WO | WO 0102810 | 1/2001 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz, vol. 85, No. 5, 1989.

"New Flowmeter Principle", by: Walt Boyes—Published in Flow Controls Magazine—Oct. 2003 Issue.

"Piezoelecric Polymers" by: J.S. Harrison—ICASE Report, Dec. 2001.

Sonar-Based Volumetric Flow Meter for Chemical and Petrochemical Applications by: Daniel L. Gysling and Douglas H. Loose—Feb. 14, 2003.

"Sound and Sources of Sound"by: A.P. Dowling and J.E. Williams—pp. 224-229.

"Viscous Attenuation of Acoustic Waves in Suspensions" by R.L. Gibson, Jr. and M.N. Toksoz, May 1989.

"Sound and Sources of Sound"by: A.P. Dowling and J.E. Williams—pp. 224-229 , 1983.

* cited by examiner

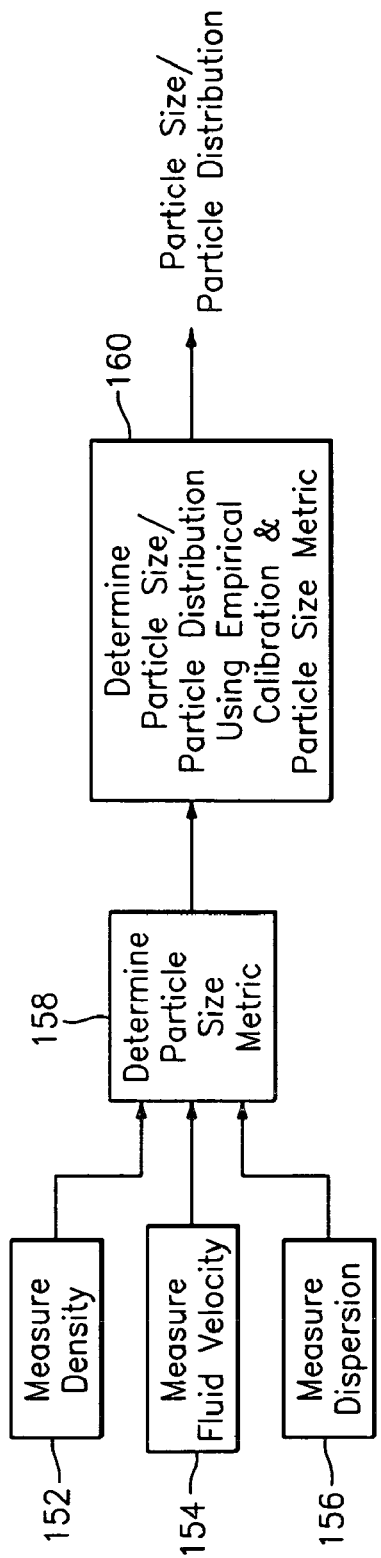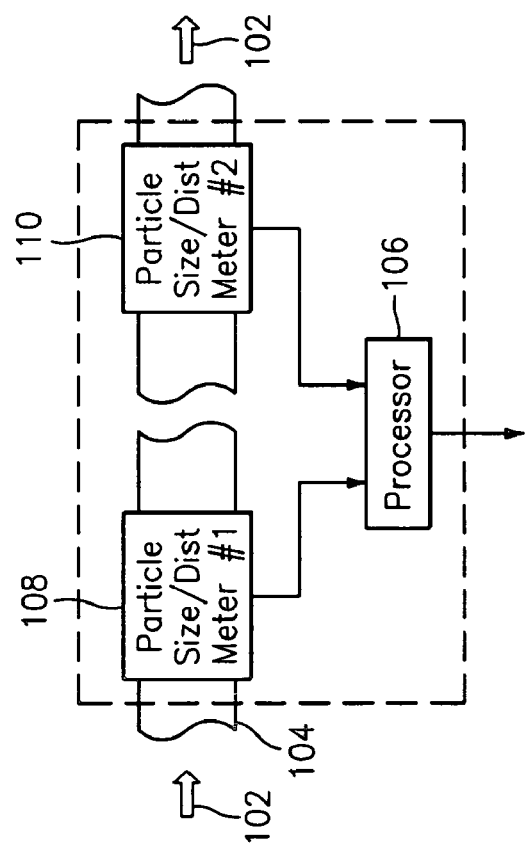

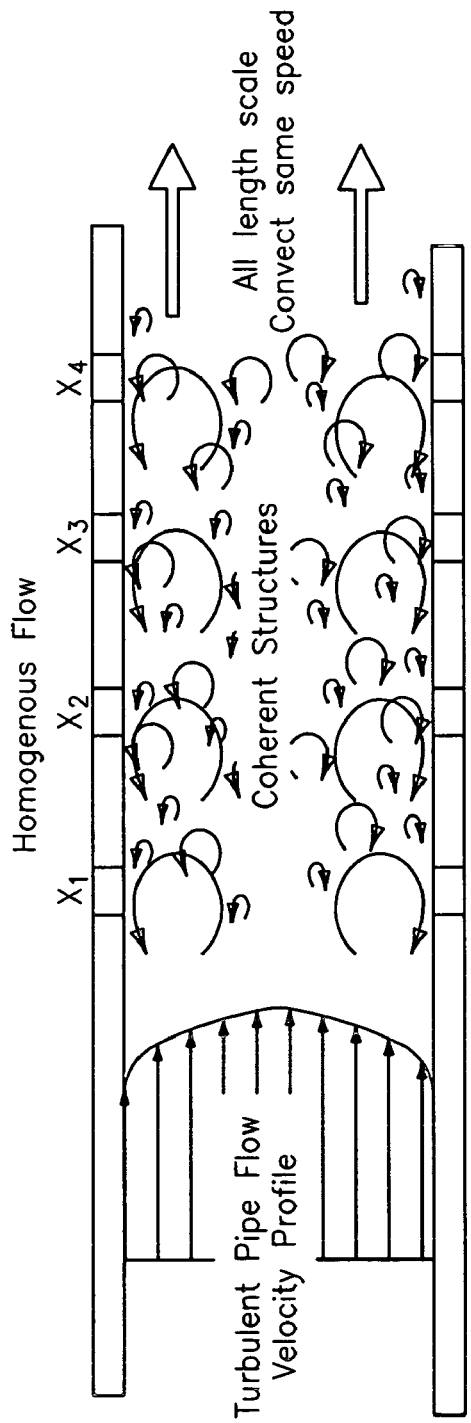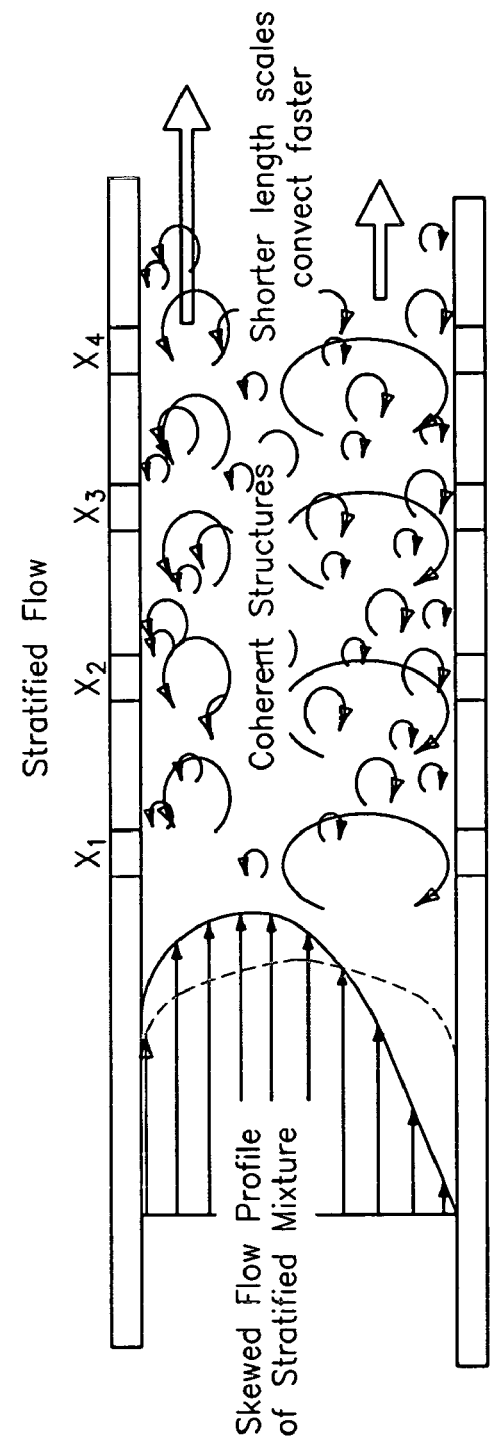
FIG. 4a
FIG. 4b

METHOD AND APPARATUS FOR DETECTING AND CHARACTERIZING PARTICLES IN A MULTIPHASE FLUID

CROSS-REFERENCE TO RELATED PATENT APPLICATIONS

The present application claims the benefit of U.S. Patent Application No. 60/681,925, filed on May 16, 2005; and is related to U.S. Provisional Patent Application No. 60/552,164, filed Mar. 10, 2004 and U.S. patent application Ser. No. 11/077,709, filed Mar. 10, 2005, each of which is incorporated by reference herein in its entirety.

TECHNICAL FIELD

This invention relates generally to measuring the parameters of particles within a multiphase fluid and more particularly to a method and apparatus for measuring the size and distribution of particles within a multiphase fluid flowing within a pipe.

BACKGROUND OF THE INVENTION

Many industrial fluid flow processes involve the transportation of a high mass fraction of high density, solid materials through a pipe. For example, a process known as hydrotransport is used in many industries to move solids from one point to another. In this process, water is added to the solids and the resulting mixture is pumped through typically large diameter pipes.

The operation of a hydrotransport line typically involves some degree of stratification, where flow velocity near the bottom of the pipe is less than flow velocity near the top of the pipe. The level of stratification in this flow (i.e., the degree of skew in the velocity profile from the top of the pipe to the bottom of the pipe) is dependent upon numerous material and process parameters, such as flow rate, density, pipe size, particle size, and the like. If the level of stratification extends to the point where deposition velocity is reached, the solids begin to settle to the bottom of the pipe, and if the condition is undetected and persists, complete blockage of the pipe can occur, resulting in high costs associated with process downtime, clearing of the blockage, and repair of any damaged equipment. As such, information regarding the size and distribution of the particles within the flow would not only allow for the efficiency of the system to be characterized, but would also allow for the detection of problems within the system. For example, knowing the particle size would allow for the velocity of the flow within the hydrotransport line to be tailored to a particular particle size. Additionally, knowing the distribution of the particles within the flow would allow problems, such as blockage and sanding, to be detected.

To reduce the chance of a costly blockage formation, current practice is to operate the pipeline at a flow velocity significantly above the critical deposition velocity. However, this technique has two significant drawbacks due to operating at higher velocities. First, it causes higher energy usage due to higher friction losses and second, it causes higher pipe wear due to abrasion between the solids and the inner surface of the pipe. This technique may also be undesirable due to high water consumption. A reliable means of measuring parameters such as velocity, level of stratification, and volumetric flow rate of a stratified flow would enable the operation of the pipeline at a lower velocity, resulting in an energy savings and a lower pipe wear.

Various technologies exist for measuring the physical parameters of an industrial flow process. Such physical parameters may include, for example, volumetric flow rate, composition, consistency, density, and mass flow rate. While existing technologies may be well-suited for aggressive, large diameter flows, these technologies may be unsuitable for stratified flows, which can adversely affect accuracy in measuring physical parameters of the flow.

Several non-commercial techniques for determining the onset of solids deposition in slurry pipelines are described in recent literature. For example, one technique uses a commercial clamp-on ultrasonic flow meter, in Doppler mode, with coded transmissions and cross-correlation detection, wherein the detection point for the meter is set at a certain pipe level, e.g., 10% above the pipe invert (i.e., the pipe bottom for horizontal pipes). Cross-correlation of a time-gated ultrasonic return signal enables detection of reflected signals only from the set point and a decrease in coherence between the transmitted and received signals indicates unsteady flow conditions due to solids deposition.

Another existing non-commercial technique measures the apparent electrical resistivity of the slurry near the pipe invert, with a change in resistivity indicating the formation of a solids bed. This technique was deemed to be not very successful due to poor repeatablility and other problems.

Still another non-commercial technique utilizes self-heating thermal probes mounted in the slurry. A moving slurry removes temperature from the probes, while a stationary solids bed around the probe causes heat to build up within the probes. Thus a temperature rise is indicative of solids deposition. While this technique is promising, it is an invasive technique requiring the thermal probes to be placed within the pipe. Such invasive techniques have drawbacks in that they require the process to be stopped to allow for installation and maintenance of the probes.

Yet another technique involves the installation of a short pipe with a slightly larger inside diameter, where a stationary solids bed is allowed to form and is maintained as a control while the main pipeline is operated with no solids bed. The control solids bed is then monitored by one or more of the techniques described above. An increase in the height of the control bed then indicates the likely formation of a sliding bed in the main pipeline, which is a precursor of a stationary bed and an eventual blockage. When the control solids bed height increases beyond a certain limit, the flow rate may be increased to avoid solids deposition. To date, each of the methods described hereinabove remain undesirable due to either poor repeatability, poor accuracy or difficult and costly implementation.

SUMMARY OF THE INVENTION

An industrial meter for measuring the size and distribution of particles within a fluid flowing within a pipe is provided, wherein the industrial meter includes at least one metering device for determining at least one of the mixture density of the fluid, the flow rate of the fluid and the dispersion of the fluid and wherein the at least one metering device generates meter data responsive to at least one of the mixture density of the fluid, the flow rate of the fluid and the dispersion of the fluid. Additionally, a processing device is provided, wherein the processing device is communicated with the at least one metering device such that the processing device receives and processes the meter data to generate fluid information responsive to the size and distribution of the particles within the fluid.

Moreover, a method for measuring the size and distribution of particles within a multiphase fluid flowing within a pipe is provided, wherein the method includes selecting an initial velocity of the fluid and responsive to said initial velocity, determining a first frequency range within the fluid. The method also includes identifying a convective ridge within the fluid for the first frequency range and calculating a nominal velocity of the fluid for the first frequency range. Moreover, the method includes dividing the first frequency range into a plurality of second frequency ranges, determining an average convection velocity for each of the plurality of second frequency ranges and for each of the plurality of second frequency ranges, determining a nominal convection velocity of coherent structures having a range of length scales corresponding to the second frequency range. Furthermore, the method includes normalizing the nominal convection velocity for each of the plurality of second frequency ranges and determining a level of dispersion for the fluid.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike:

FIG. 3a is block diagram of the method of determining the particle size and/or particle distribution of a multiphase fluid in accordance with the present invention.

FIG. 3b is a schematic diagram of a system for determining the efficiency of the processing of particles (e.g., such as breaking up of rocks) within a multiphase fluid flow within a pipe (such as a hydrotransport line).

FIG. 4a is the turbulent pipe flow velocity profile of a homogeneous flow.

FIG. 4b is the skewed or dispersed flow velocity profile of a stratefied flow.

DETAILED DESCRIPTION OF THE INVENTION

Figure 1:
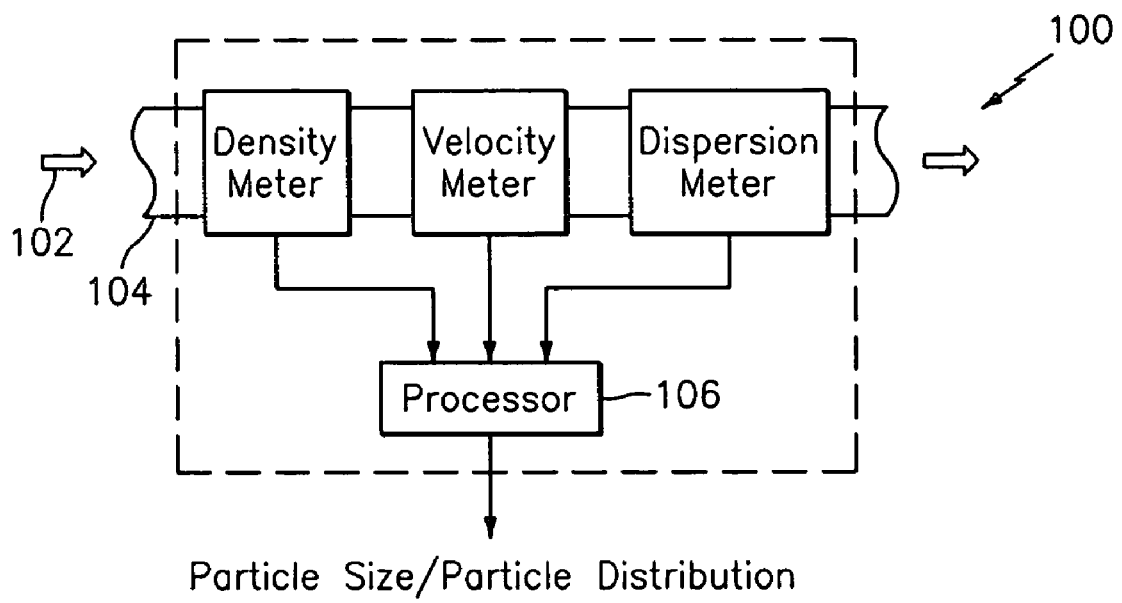
FIG. 1 is a schematic diagram of a particle size and/or particle distribution monitor in accordance with the present invention.

Referring to FIG. 1, one embodiment of a monitoring apparatus 100 for measuring the particle size and/or particle distribution of a multiphase fluid 102 flowing within a pipe 104 is illustrated, wherein the particle size and/or particle distribution measurement is a relative measurement of the size and distribution of particles within the multiphase fluid 102. The apparatus 100 may include at least one device that measures parameters of the fluid 102, such as the mixture (or fluid) density of the fluid 102, the average flow rate of the fluid 102 and the dispersion of the fluid 102. These parameters may then be communicated to a processor 106 which determines a particle size metric via the method shown in FIG. 3a, wherein the particle size metric may be indicative of the relative size and/or distribution of the particles within the fluid flow 102, as discussed further hereinafter. It should be appreciated that the size and/or particle distribution can be quantified using empirical data to calibrate the particle metric to a definitive parameter of the fluid 102 flow as shown in FIG. 3a. It should be further appreciated that the density of the fluid may be measured using any known density meter, such as via a coriolis meter and a nuclear densitometer, and the average velocity of the fluid flow may be measured using any known flow meter, such as via a magmeter and a venturi meter and the dispersion of the mixture may be measured using any known dispersion meter.

Figure 2:
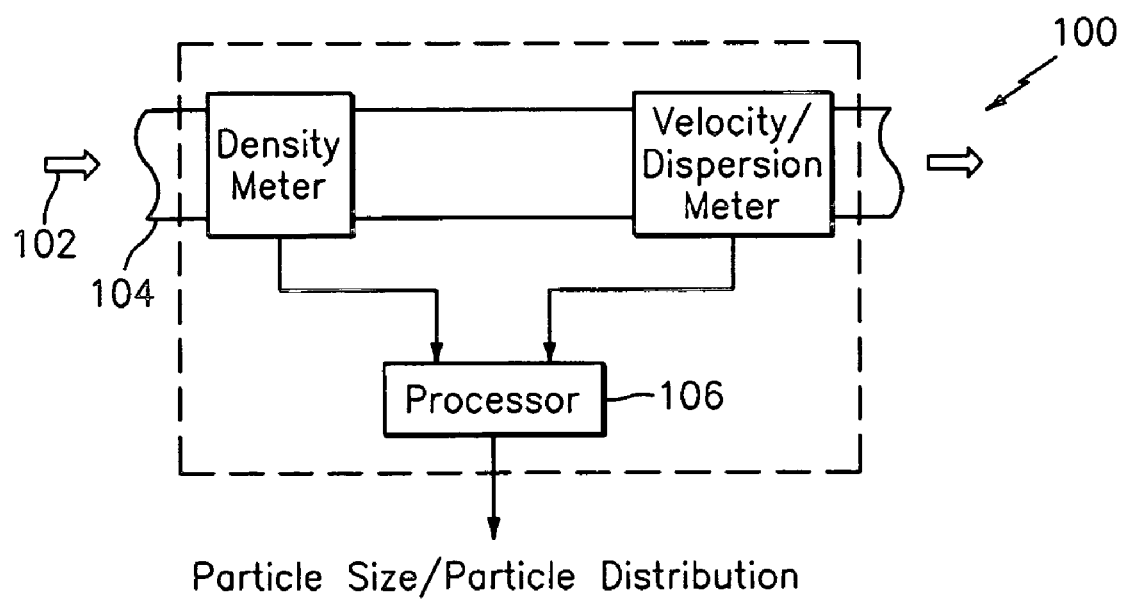
FIG. 2 is schematic diagram of another embodiment of a particle size and/or particle distribution monitor in accordance with the present invention.
Figure 11:
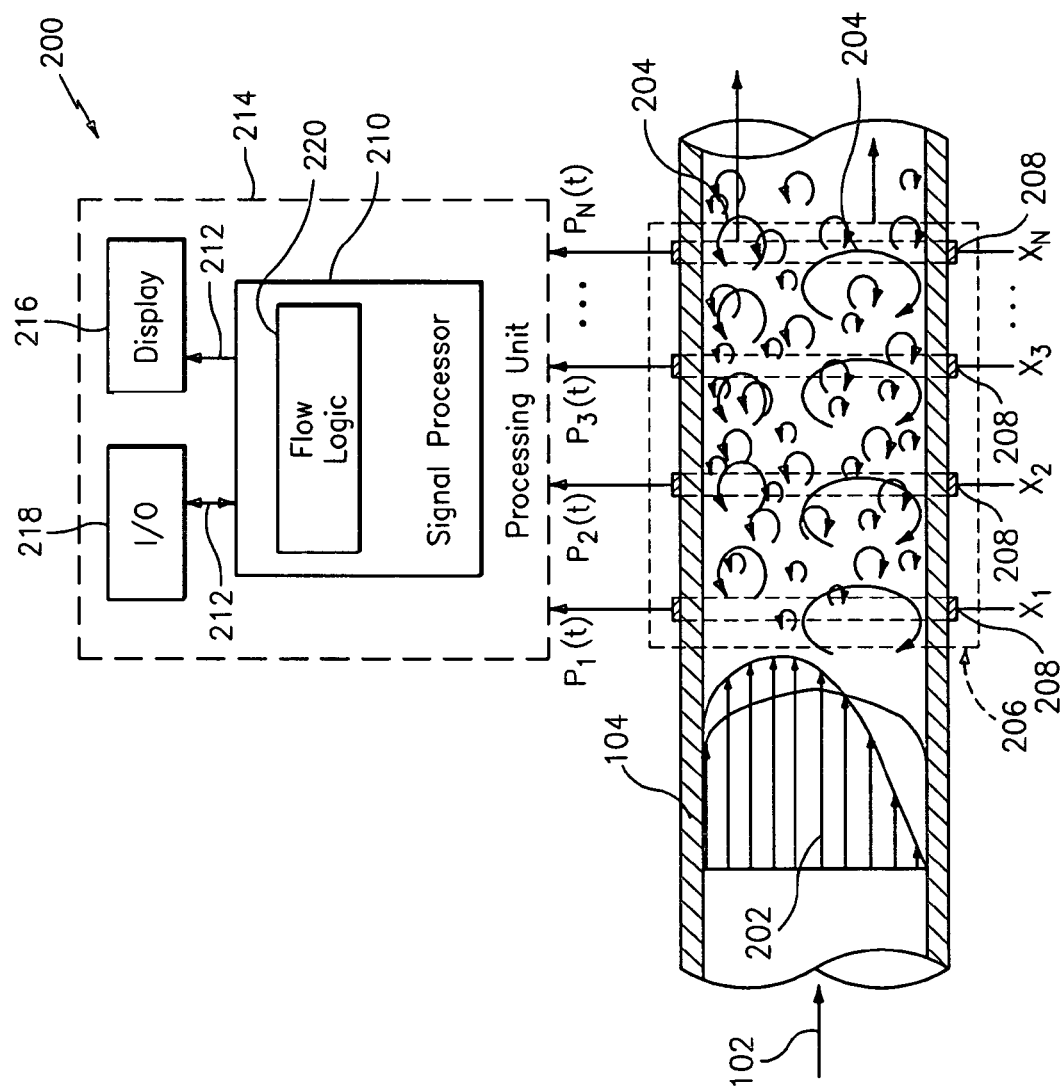
FIG. 11 is schematic diagram of an apparatus for determining at least one parameter associated with a stratified fluid flowing in a pipe in accordance with the present invention.
Figure 14:
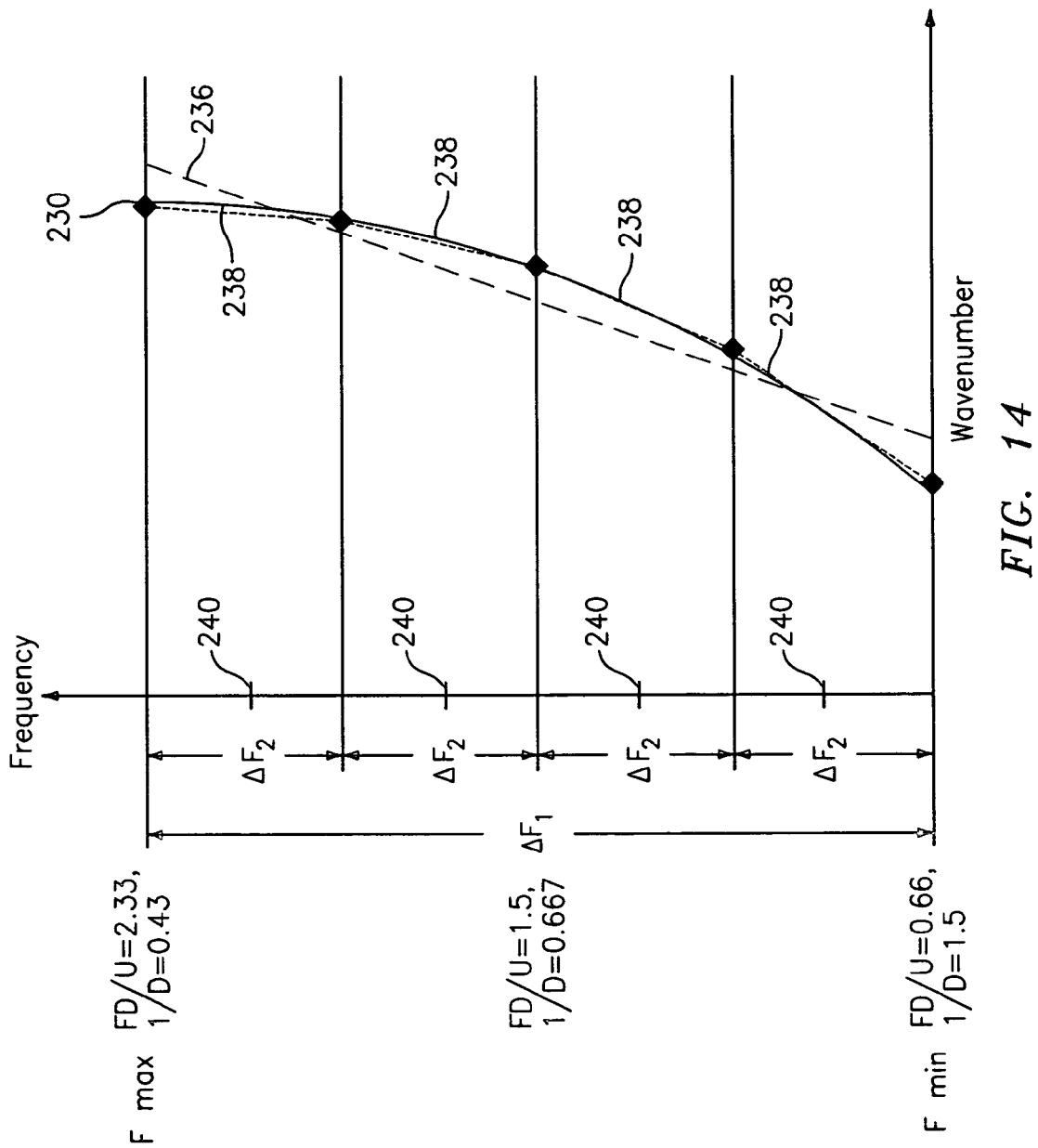
FIG. 14 is a k-ω plot of data processed from an apparatus embodying the present invention that illustrates a non-linear ridge in the k-ω plot, as may be found with dispersive flow.
Figure 15:
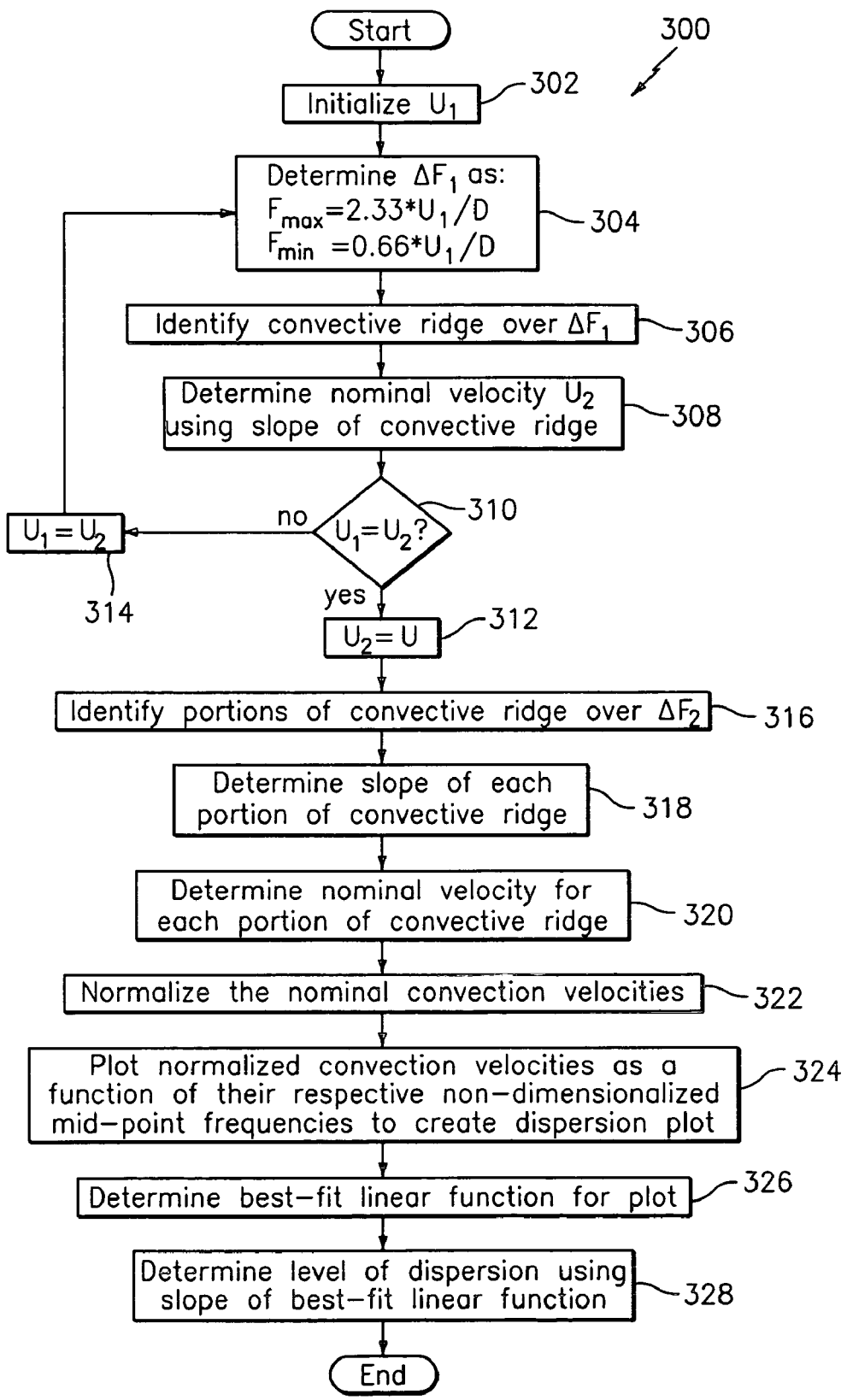
FIG. 15 is a flow chart depicting a method of quantifying the level of stratification in accordance with the present invention.

The present invention describes such a dispersion meter as will be discussed in greater detail hereinafter. One embodiment of an apparatus that measures dispersion of the fluid 102 is shown in FIGS. 11, 14 and 15, and other embodiments for a dispersion and flow rate meter are shown in FIGS. 23-28. Furthermore, referring to FIG. 2 an additional embodiment of a monitoring apparatus 100 for measuring the particle size and/or particle distribution of a multiphase fluid 102 flowing within a pipe 104 is illustrated wherein the velocity and dispersion of the fluid 102 may be measured using a single apparatus similar to that as illustrated in FIGS. 11, 14, and 15.

Referring once again to FIG. 3a, a high level block diagram illustrating a method 150 for determining the particle size and/or particle distribution of particles within the fluid flow 102 is shown. The method 150 includes measuring the density, fluid velocity and dispersion of the fluid flow 102, as shown in blocks 152, 154 and 156, respectively. These measurement values are then used to determine the particle size metric, as shown in block 158, responsive to the following mathematical relationship, $$\Gamma = f(\Delta, \rho_{mix}, V)$$

Wherein $\Delta$ is the dispersion metric, $\rho_{mix}$ is the mixture specific gravity or density of the flow 102, and V is the average mixture velocity in ft/sec. The particle size and/or particle distribution may be then be determined using the particle size metric $\Gamma$ and an empirical calibration approach, as shown in block 160, wherein an increasing $\Gamma$ value would correlate with an increasing particle size.

Referring to FIG. 3b, a system 500 for determining characteristics and efficiency related to the processing of the multiphase fluids 102 is illustrated, wherein the mixture 102 is flowed through a hydrotransport line or other piping 104 to crush or otherwise break up the rocks into smaller rocks as the rocks flow through the pipe 104. As shown, the particle size and/or particle distribution is measured at two separate points along the pipe 104 via a first monitor 108 and a second monitor 110, wherein the reading from each of the monitors 108, 110 are provided to a processor 106 which compares the particle size at each location and provides a signal indicative of the efficiency or amount of reduction in the size of the rocks or particles flowing within the pipe 104. The efficiency of the system may be determined by comparing the particle size and/or particle distribution at the second monitor 110 with the particle size and/or particle distribution at the first monitor 108. If the particles have not decreased in size to a desired level, then the system may be adjusted to accommodate (i.e. take steps to produce a greater decrease in particle size between the first monitor 108 and the second monitor 110). The following provides a description of different embodiments of an apparatus for measuring the velocity of the fluid flow 102 and/or the dispersion (e.g., stratification) of the fluid flow 102, which can be used in the embodiments shown in FIGS. 1 to 3b.

Figure 5A:
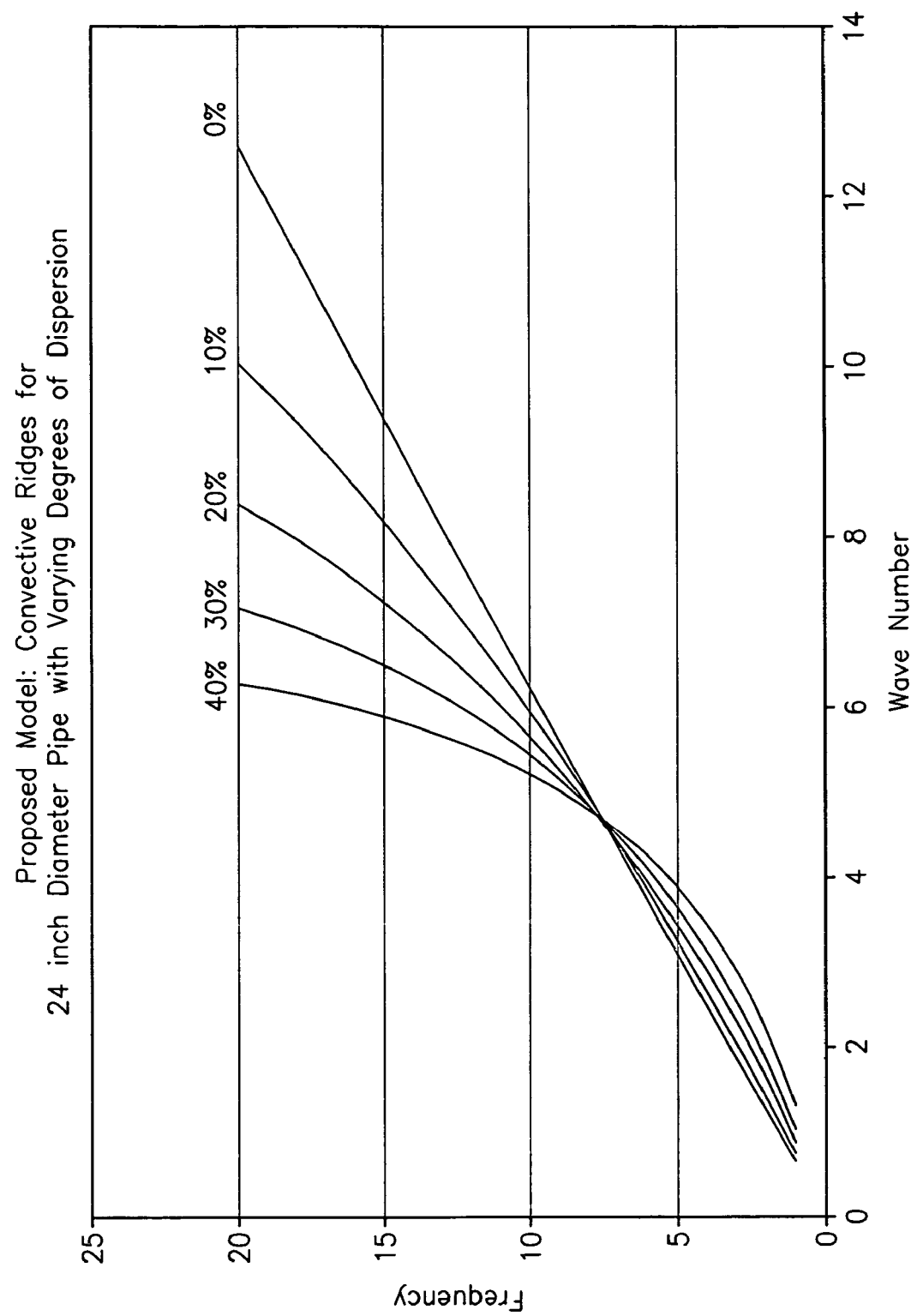
FIG. 5a is a plot of a plurality of convective ridges in the k-ω plane of different fluids having different dispersion characteristics in accordance with the present invention.
Figure 5B:
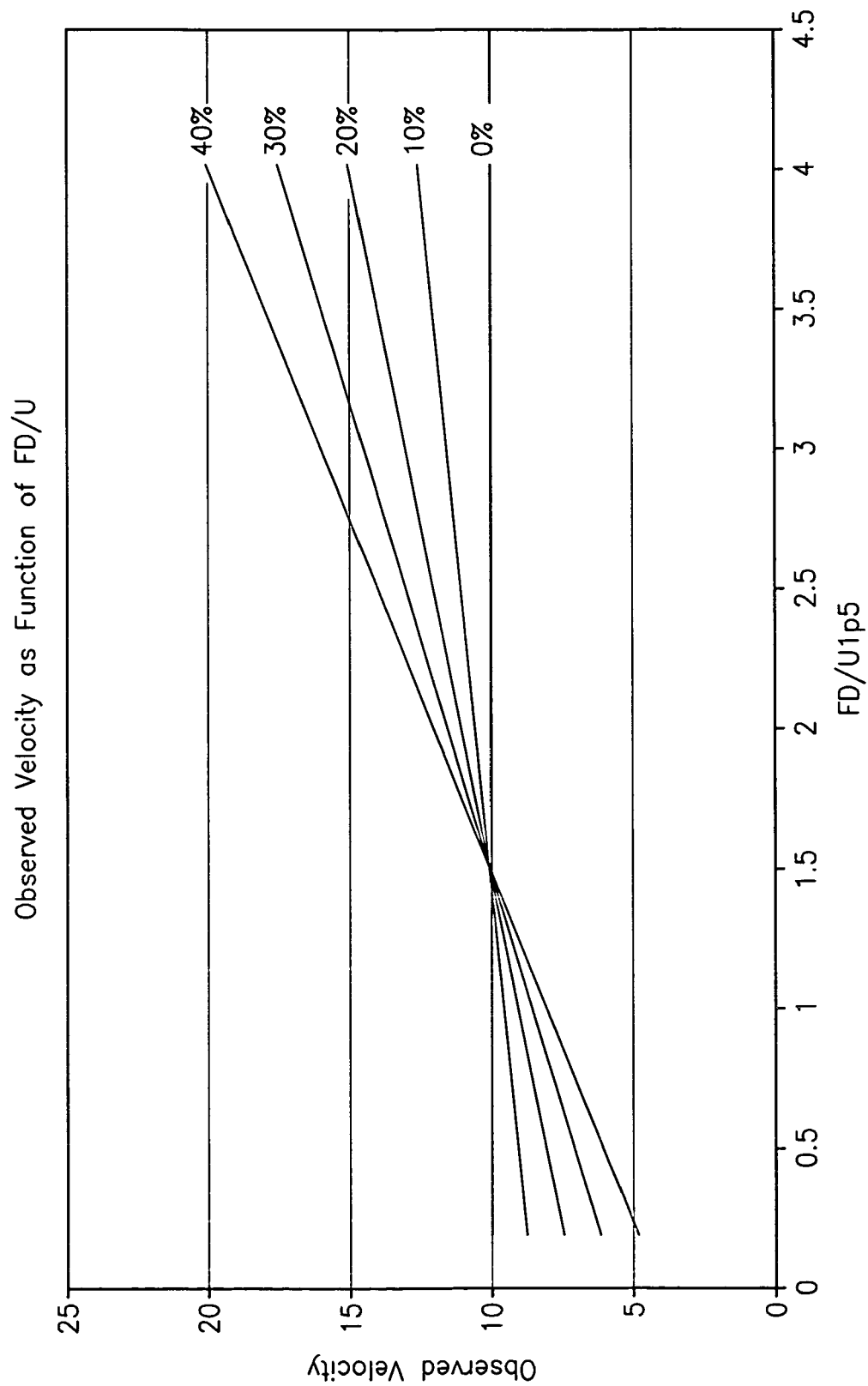
FIG. 5b is a plot of a plurality of observed velocities as a function of FD/U of different fluids having different dispersion characteristics in accordance with the present invention.
Figure 6:
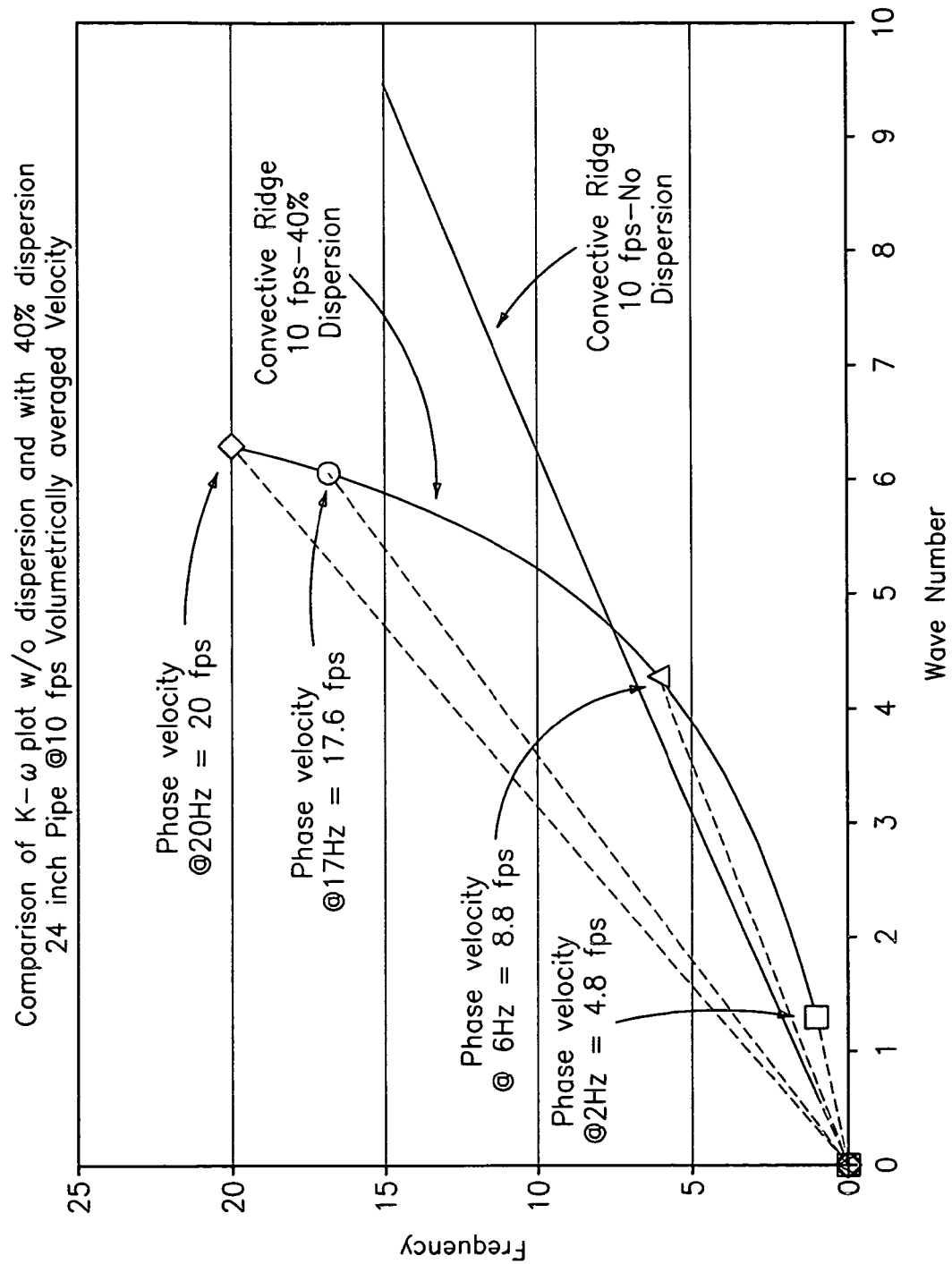
FIG. 6 is a plot of the convective ridges in the k-ω plane of a fluid having no dispersion and a fluid having 40% dispersion in accordance with the present invention.

Referring to FIG. 4a, a side view of a pipe having a homogenous fluid flow within is shown. As can be seen, the coherent structures within the flow convect evenly (i.e. at the same speed) across the diameter of the pipe. However, referring to FIG. 4b, a side view of a pipe having a stratified fluid flow within is shown. In contrast to the homogenous fluid flow of FIG. 4a, the coherent structures within the stratified fluid flow do not convect evenly across the diameter of the pipe. As such, the coherent structures near the top of the pipe convect faster than the coherent structures near the bottom of the pipe. Referring to FIG. 5a, a proposed model illustrates convective ridges in the k-ω plane for a several different types of fluid flow within a 24 inch diameter pipe having varying degrees of dispersion. Referring to FIG. 5b, the observed velocity of the fluid flow as a function of the FD/U for several different fluids having different dispersion characteristics is shown. Moreover, referring to FIGS. 6a and 6b, plots showing a comparison of the convective ridges in the k-ω plane for a fluid flowing within a 24 inch pipe at 10 feet/sec (volumetrically averaged velocity) without dispersion versus with 40% dispersion is shown.

Figure 7:
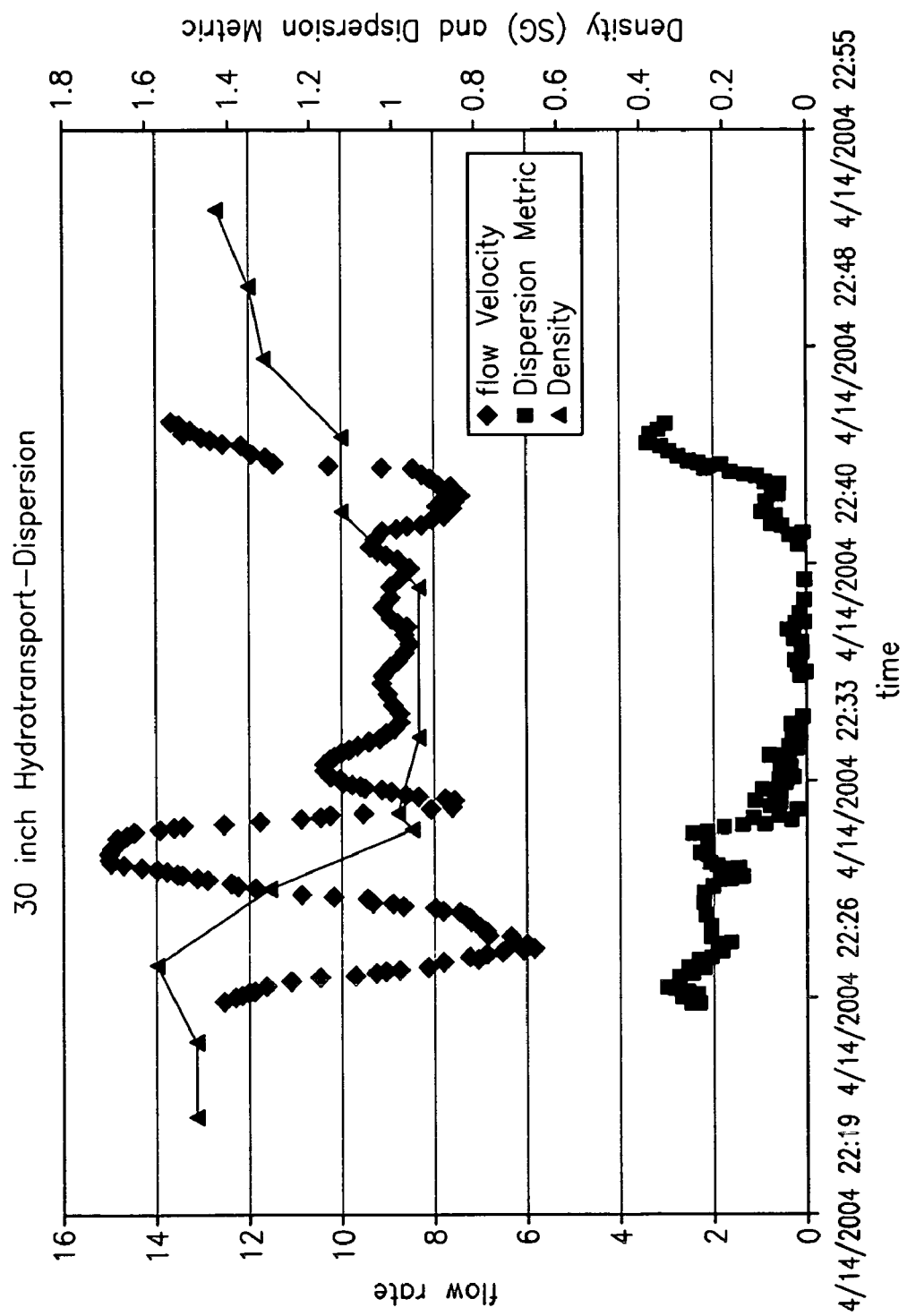
FIG. 7 is a plot of the measured flow velocity, density and dispersion metric of a multiphase fluid flowing within a 30 inch hydrotransport line, which is illustrative of the relationship between these parameters in accordance with the present invention.
Figure 8A:
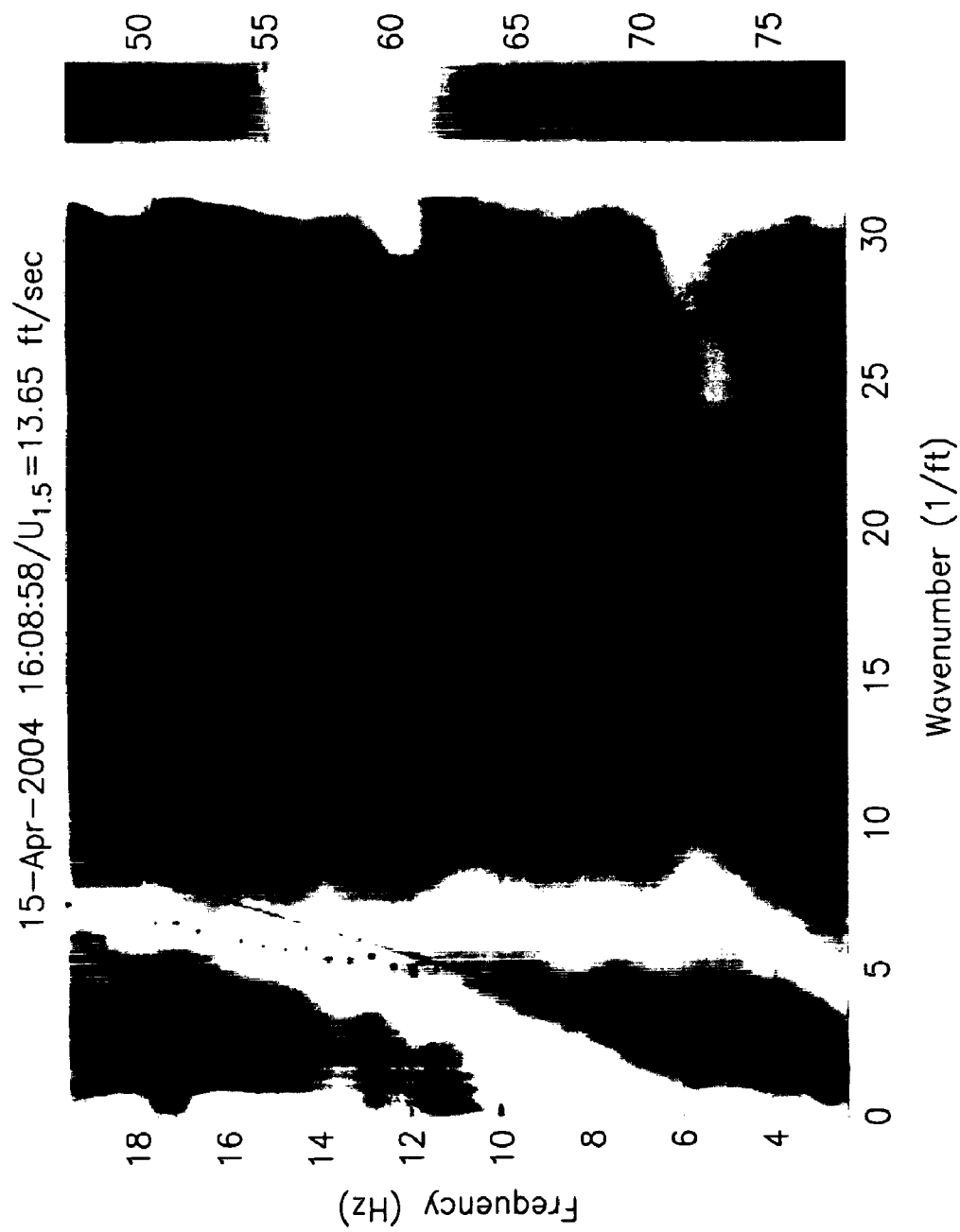
FIG. 8a is a plot of the convective ridge in the k-ω plane of a fluid having dispersion in accordance with the present invention.
Figure 8B:
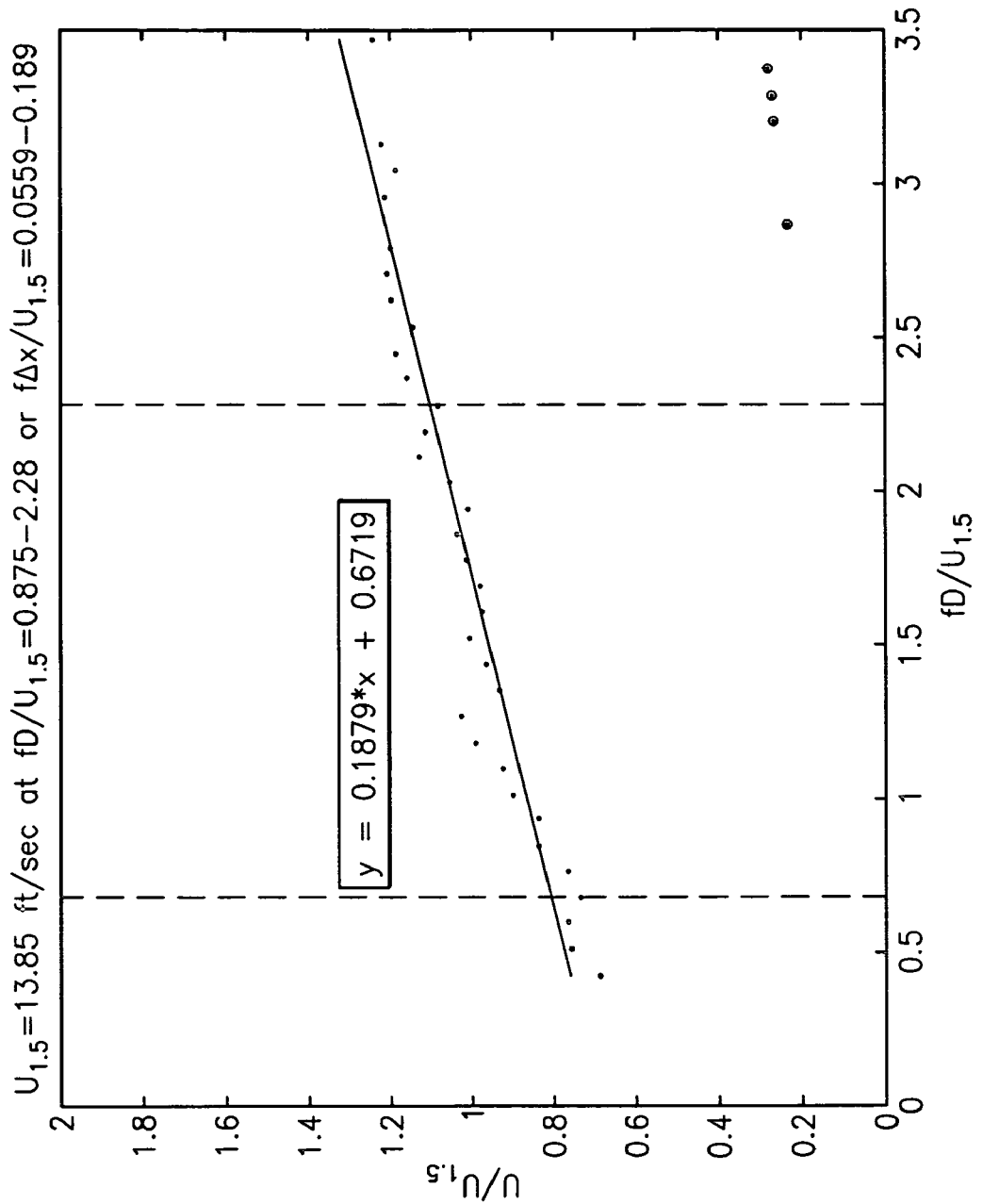
FIG. 8b depicts an example of a dispersion plot for convective ridge of FIG. 8a in accordance with the present invention.
Figure 8C:
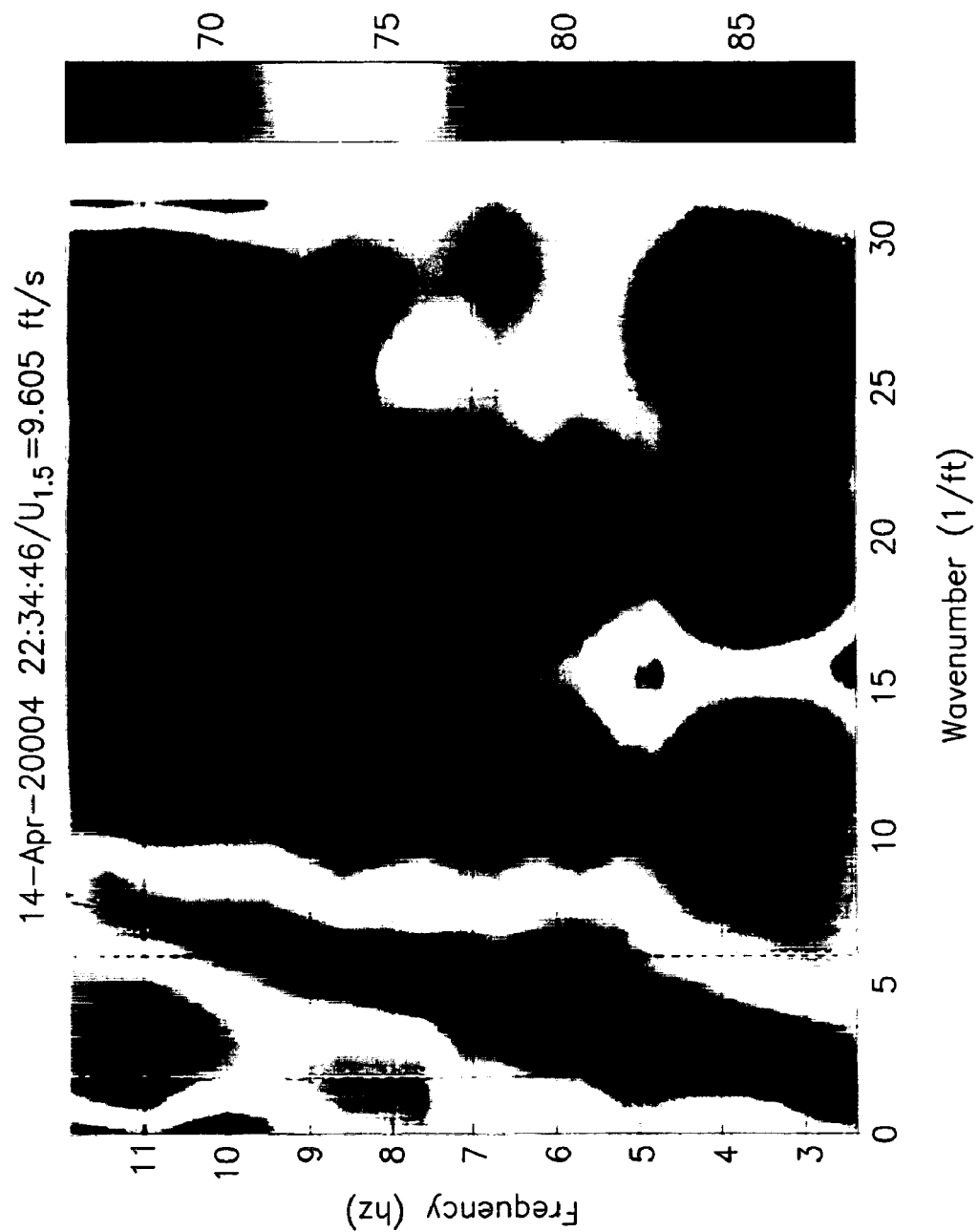
FIG. 8c is a plot of the convective ridge in the k-ω plane of a fluid having minimal dispersion in accordance with the present invention.
Figure 8D:
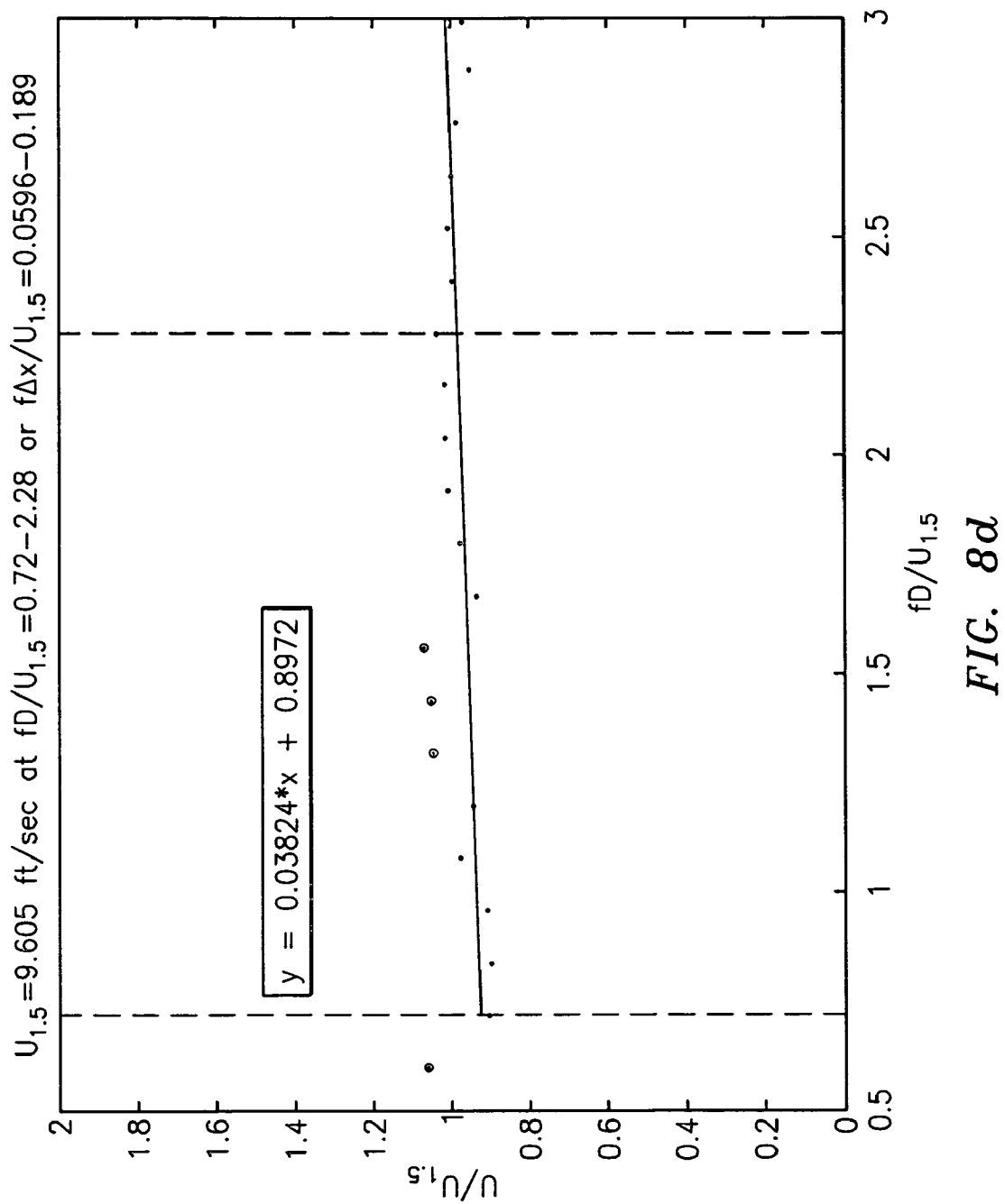
FIG. 8d depicts an example of a dispersion plot for convective ridge of FIG. 8c in accordance with the present invention.
Figure 9:
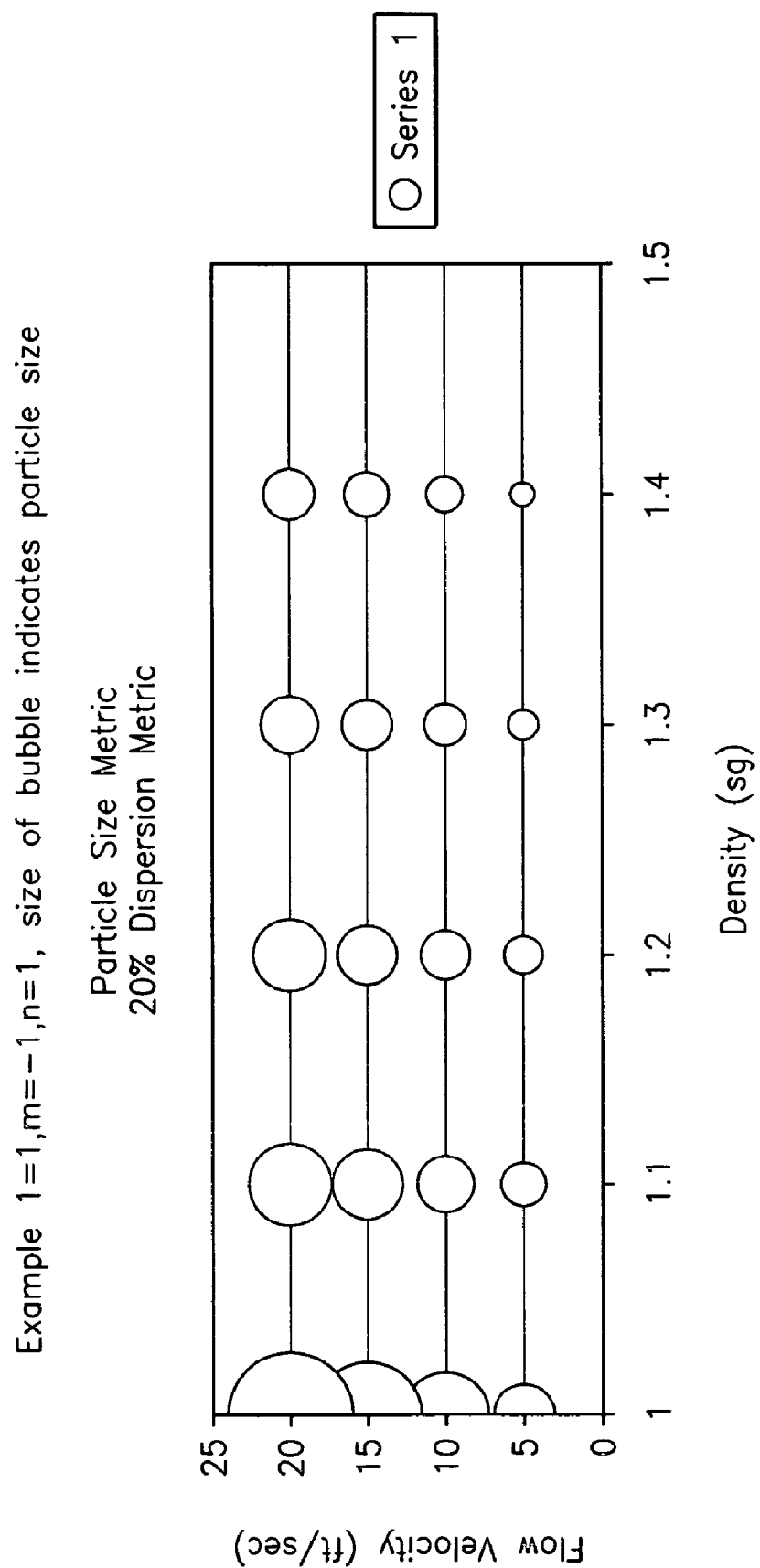
FIG. 9 is a diagram illustrative of the relationship of the average flow velocity, mixture density, and dispersion in determining the particle size metric in accordance with the present invention.
Figure 10:
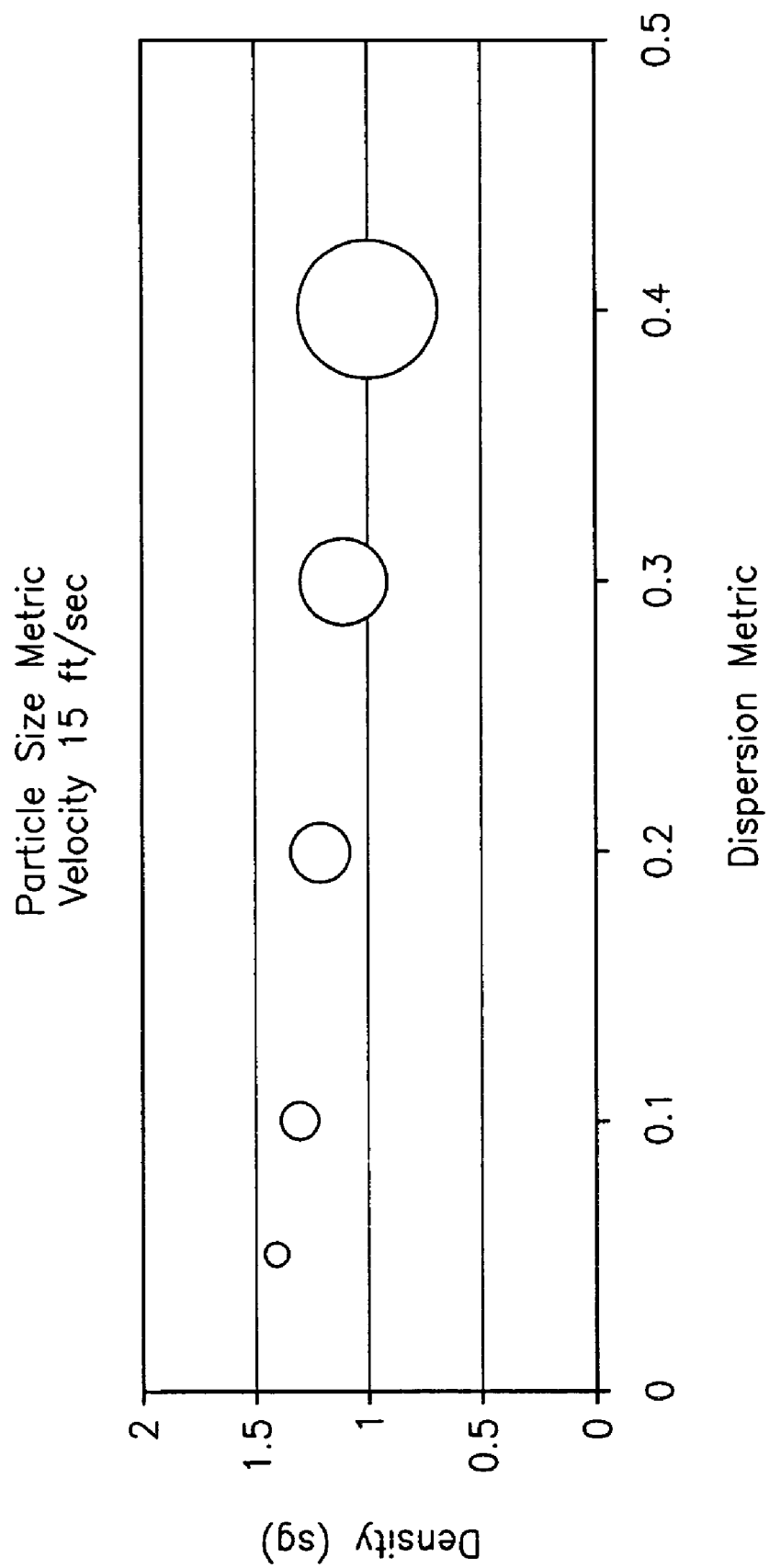
FIG. 10 is another diagram illustrative of the relationship of the average flow velocity, mixture density, and dispersion in determining the particle size metric in accordance with the present invention.

Referring to FIG. 7, a plot of the measured flow velocity, density and dispersion metric for a multiphase fluid flowing within a 30 inch hydrotransport line is shown and illustrates the relationship between the measured flow velocity, the density and the dispersion metric. FIG. 8a shows one example of a plot of the convective ridge in the k-ω plane for a fluid flowing within a pipe having dispersion and FIG. 8b shows an example of a dispersion plot for the convective ridge in FIG. 8a. FIG. 8c shows another example of a plot of the convective ridge in the k-ω plane for a fluid flowing within a pipe having minimal dispersion and FIG. 8d shows an example of a dispersion plot (i.e. dispersion metric) for the convective ridge in FIG. 8c. As can be seen, the example in FIGS. 8a and 8b has more dispersion than the examples in FIGS. 8c and 8d. This may be correlated by the slope of the dispersion plot (i.e. dispersion metric) shown in FIG. 8b, which has a greater slope than the dispersion plot of FIG. 8d. Furthermore, referring to FIGS. 9 and 10, diagrams illustrating the relationship between the particle size within a fluid flow and the average flow velocity, the mixture density and the dispersion are shown.

As described in commonly-owned U.S. Pat. No. 6,609,069 to Gysling, entitled "Method and Apparatus for Determining the Flow Velocity Within a Pipe", and U.S. Pat. No. 6,889,532, filed on Nov. 11, 2001, which are incorporated herein by reference in their entireties, unsteady pressures along a pipe 104 caused by coherent structures (e.g., turbulent eddies and vortical disturbances) that convect with a fluid flowing within the pipe 104 contain useful information regarding parameters of the fluid 102. The present invention provides various means for using this information to measure parameters of a stratified flow, such as, for example, velocity, level/degree of stratification, and volumetric flow rate.

Referring to FIG. 11, an apparatus 200 for measuring at least one parameter associated with a flow 102 flowing within a duct, conduit or other form of pipe 104, is shown. The parameter of the flow 102 may include, for example, at least one of: velocity of the flow 102, volumetric flow rate of the flow 102, dispersion of the mixture, and level of stratification of the flow 102. In FIG. 11, the flow 102 is depicted as being stratified, where a velocity profile 202 of the flow 102 is skewed from the top of the pipe 104 to the bottom of the pipe 104, as may be found in industrial fluid flow processes involving the transportation of a high mass fraction of high density, solid materials through a pipe 104 where the larger particles travel more slowly at the bottom of the pipe 104. For example, the flow 102 may be part of a hydrotransport process.

Referring to FIGS. 11 and 4a, the flow 102 is again shown passing through the pipe 104. However, in FIG. 4a, the flow 102 is depicted as a non-stratified, Newtonian flow operating in the turbulent regime at Reynolds numbers above about 100,000. The flow 102 of FIG. 4a has a velocity profile 202 that is uniformly developed from the top of the pipe 104 to the bottom of the pipe 104. Furthermore, the coherent structures 204 in the non-stratified, turbulent, Newtonian flow 102 of FIG. 4a exhibit very little dispersion. In other words, the speed of convection of the coherent structures 204 is not strongly dependent on the physical size of the structures 204. As used herein, dispersion describes the dependence of convection velocity with wavelength, or equivalently, with temporal frequency. Flows for which all wavelengths convect at a constant velocity are termed "non-dispersive". For turbulent, Newtonian flow, there is typically not a significant amount of dispersion over a wide range of wavelength to diameter ratios.

Sonar-based flow measurement devices, such as, for example, the device described in aforementioned U.S. Pat. No. 6,609,069 to Gysling, have advantageously applied the non-dispersive characteristic of turbulent, Newtonian flow in accurately determining flow rates. For stratified flows such as those depicted in FIG. 11, however, some degree of dispersion is exhibited. In other words, the coherent structures 204 convect at velocities that depend on their size, with larger length scale coherent structures 204 tending to travel slower than smaller length scale structures 204. As a result, some of the underlying assumptions associated with prior sonar-based flow measurement devices, namely that the speed of convection of the coherent structures 204 is not strongly dependent on the physical size of the structures 204 and are affected by the presence of stratification.

The apparatus 200 of FIG. 11 accurately measures parameters such as velocity, level of stratification, and volumetric flow rate of a stratified flow 102. The apparatus 200 includes a spatial array 206 of at least two sensors 208 disposed at different axial locations $x_1 \ldots x_N$ along the pipe 104. Each of the sensors 208 provides a pressure signal P(t) indicative of the unsteady pressure created by coherent structures 204 convecting with the flow 102 within the pipe 104 at a corresponding axial location $x_1 \ldots x_N$ of the pipe 104. The pressure generated by the convective pressure disturbances (e.g., eddies 114) may be measured through strained-based sensors and/or pressure sensors. The sensors 208 provide analog pressure time-varying signals $P_1(t), P_2(t), P_3(t) \ldots P_N(t)$ to a signal processor 210, which determines the parameter of the flow 102 using pressure signals from the sensors 208, and outputs the parameter as a signal 212.

While the apparatus 200 is shown as including four sensors 208, it is contemplated that the array 206 of sensors 208 includes two or more sensors 208, each providing a pressure signal P(t) indicative of unsteady pressure within the pipe 104 at a corresponding axial location X of the pipe 104. For example, the apparatus 200 may include 2, 3, 4, 5, 6, 7, 8, 9, 10, 11, 12, 13, 14, 15, 16, 17, 18, 19, 20, 21, 22, 23, or 24 sensors 208. Generally, the accuracy of the measurement improves as the number of sensors 208 in the array 206 increases. The degree of accuracy provided by the greater number of sensors 208 is offset by the increase in complexity and time for computing the desired output parameter of the flow 102. Therefore, the number of sensors 208 used is dependent at least on the degree of accuracy desired and the desire update rate of the output parameter provided by the apparatus 200.

The signals $P_1(t) \ldots P_N(t)$ provided by the sensors 208 in the array 206 are processed by the signal processor 210, which may be part of a larger processing unit 214. For example, the signal processor 210 may be a microprocessor and the processing unit 214 may be a personal computer or other general purpose computer. It is contemplated that the signal processor 210 may be any one or more analog or digital signal processing devices for executing programmed instructions, such as one or more microprocessors or application specific integrated circuits (ASICS), and may include memory for storing programmed instructions, set points, parameters, and for buffering or otherwise storing data.

The signal processor 210 may output the one or more parameters 212 to a display 216 or another input/output (I/O) device 218, wherein the I/O device 218 may also accept user input parameters. The I/O device 218, display 216, and signal processor 210 unit may be mounted in a common housing, which may be attached to the array 206 by a flexible cable, wireless connection, or the like. The flexible cable may also be used to provide operating power from the processing unit 214 to the array 206 if necessary. To determine the one or more parameters 212 of the flow 102, the signal processor 210 applies the data from the sensors 208 to flow logic 220 executed by the signal processor 210. The flow logic 220 is described in further detail hereinafter.

Figure 12:
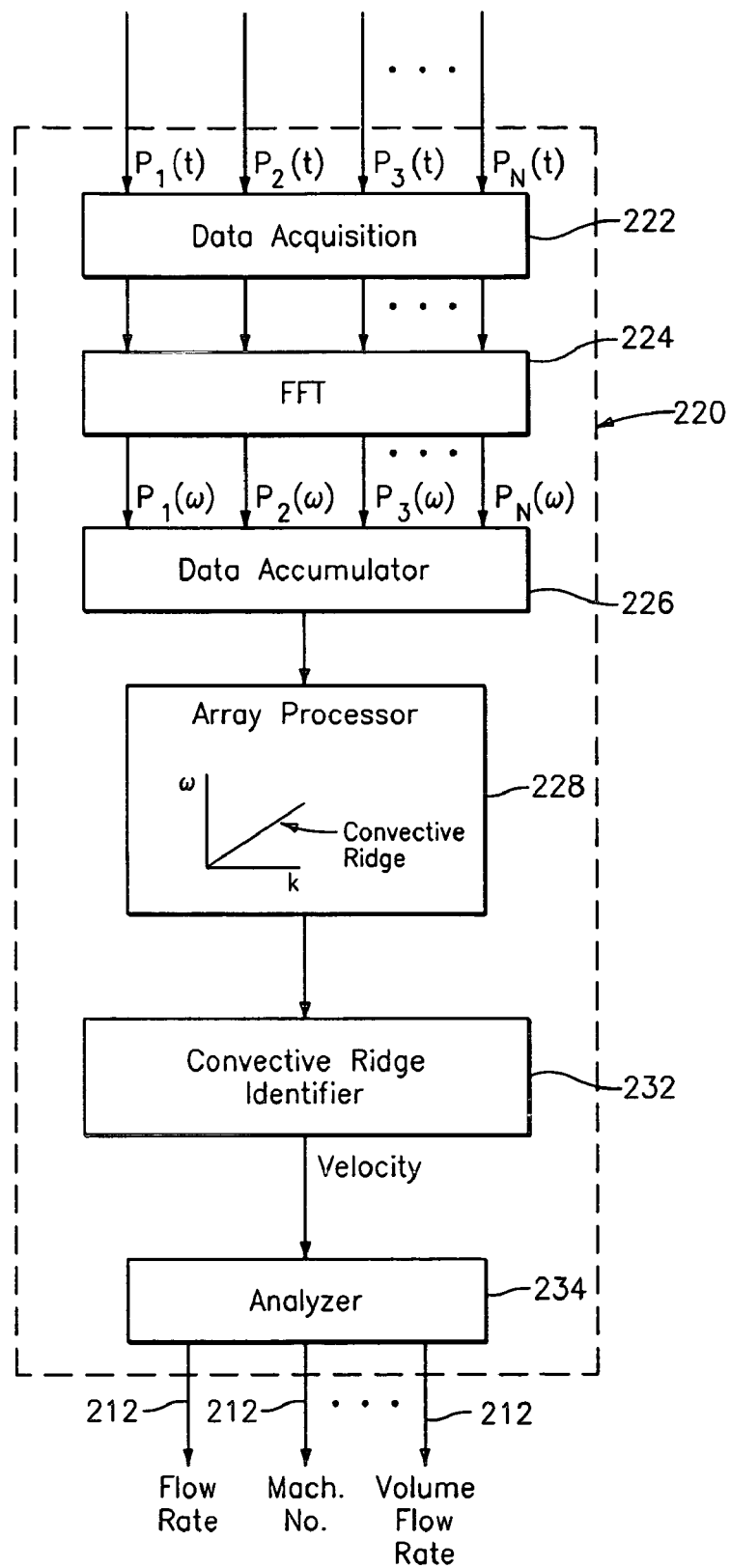
FIG. 12 is a block diagram of a flow logic used in the apparatus of the present invention.

Referring to FIG. 12, an example of the flow logic 220 is shown. It should be appreciated that some or all of the functions within the flow logic 220 may be implemented in software (using a microprocessor or computer) and/or firmware, or may be implemented using analog and/or digital hardware, having sufficient memory, interfaces, and capacity to perform the functions described herein. The flow logic 220 includes a data acquisition unit 222 (e.g., A/D converter) that converts the analog signals $P_1(t) \ldots P_N(t)$ to respective digital signals and provides the digital signals $P_1(t) \ldots P_N(t)$ to FFT logic 224. The FFT logic 224 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals. Instead of FFT's, any other technique for obtaining the frequency domain characteristics of the signals $P_1(t)-P_N(t)$, may be used. For example, the cross-spectral density and the power spectral density may be used to form a frequency domain transfer functions (or frequency response or ratios) discussed hereinafter.

One technique of determining the convection velocity of the coherent structures (e.g., turbulent eddies) 204 within the flow 102 is by characterizing a convective ridge of the resulting unsteady pressures using an array of sensors or other beam forming techniques, similar to that described in U.S. patent application Ser. No. 09/729,994, filed Dec. 4, 2000, now U.S. Pat. No. 6,609,069, which is incorporated herein by reference. A data accumulator 226 accumulates the frequency signals $P_1(\omega)-P_N(\omega)$ over a sampling interval, and provides the data to an array processor 228, which performs a spatial-temporal (two-dimensional) transform of the sensor data, from the x-t domain to the k-ω domain, and then calculates the power in the k-ω plane, as represented by a k-ω plot. The array processor 228 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

It should be appreciated that the prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensors 208 apart from each other and yet still be within the coherence length.

Convective characteristics or parameters have a dispersion relationship that can be approximated by the straight-line equation, $$k=\omega/u,$$

where u is the convection velocity (flow velocity). A plot of k-$\omega$ pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. As will be described hereinafter, as the flow becomes increasingly dispersive, the convective ridge becomes increasingly non-linear. What is being sensed are not discrete events of coherent structures 204, but rather a continuum of possibly overlapping events forming a temporally stationary, essentially white process over the frequency range of interest. In other words, the convective coherent structures 204 are distributed over a range of length scales and hence temporal frequencies.

Figure 13:
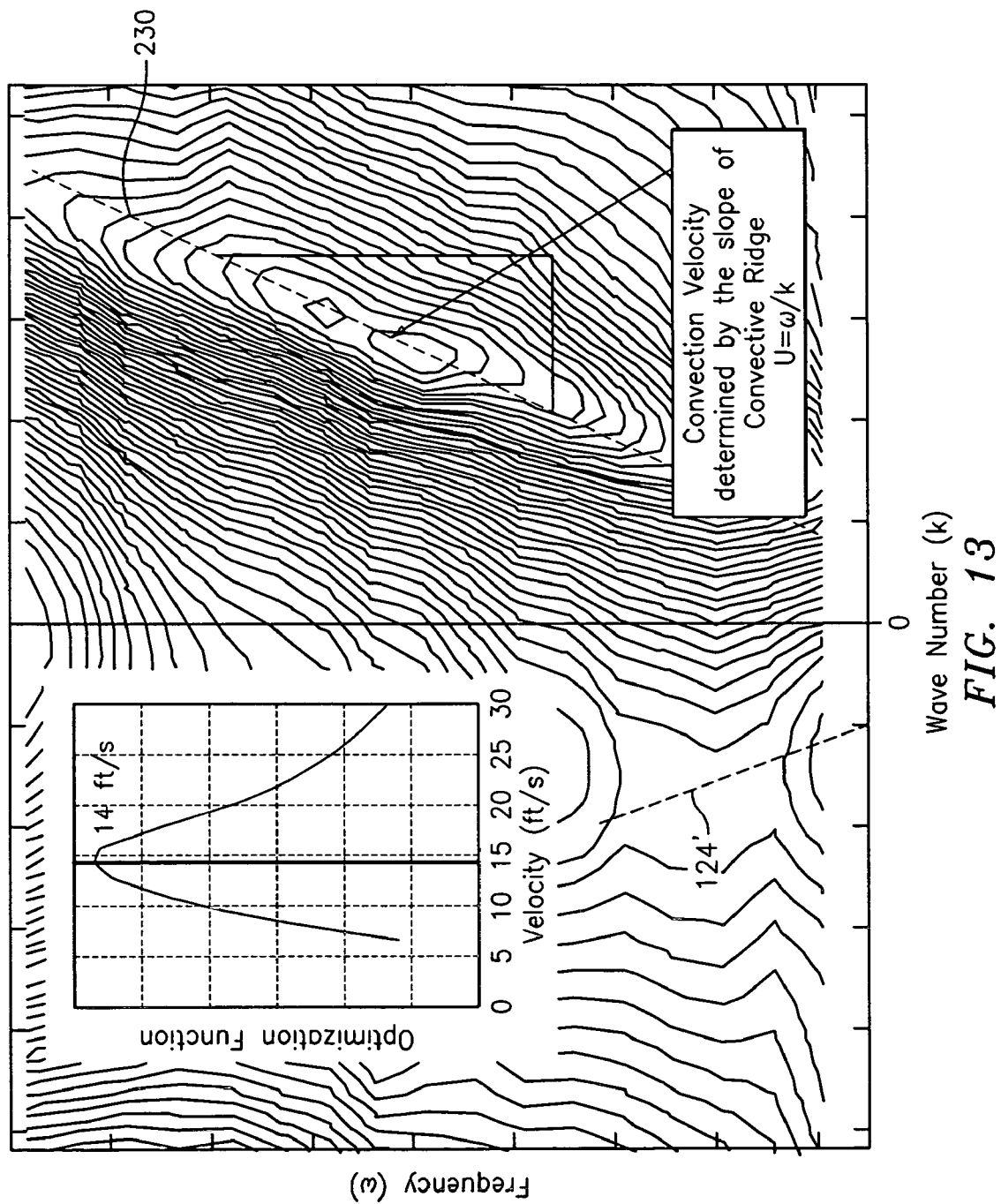
FIG. 13 is a k-ω plot of data processed from an apparatus embodying the present invention that illustrates slope of the convective ridge, and a plot of the optimization function of the convective ridge.

To calculate the power in the k-$\omega$ plane, as represented by a k-$\omega$ plot (see FIG. 13) of either the signals, the array processor 228 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of arrays of sensors 206. The present embodiment may use temporal and spatial filtering to precondition the signals to effectively filter out the common mode characteristics, Pcommon mode and other long wavelength (compared to the sensor spacing) characteristics in the pipe 104 by differencing adjacent sensors 208 and retain a substantial portion of the stochastic parameter associated with the flow field and any other short wavelength (compared to the sensor spacing) low frequency stochastic parameters. In the case of suitable coherent structures 204 being present, the power in the k-$\omega$ plane shown in the k-$\omega$ plot of FIG. 13 shows a convective ridge 230. The convective ridge 230 represents the concentration of a stochastic parameter that convects with the flow and is a mathematical manifestation of the relationship between the spatial variations and temporal variations described above. Such a plot will indicate a tendency for k-$\omega$ pairs to appear more or less along a line 230 with some slope, the slope indicating the flow velocity.

Once the power in the k-$\omega$ plane is determined, a convective ridge identifier 232 uses one or another feature extraction method to determine the location and orientation (slope) of any convective ridge 230 present in the k-$\omega$ plane. In one embodiment, a so-called slant stacking method is used, a method in which the accumulated frequency of k-$\omega$ pairs in the k-$\omega$ plot along different rays emanating from the origin are compared, each different ray being associated with a different trial convection velocity (in that the slope of a ray is assumed to be the flow velocity or correlated to the flow velocity in a known way). The convective ridge identifier 232 may accumulate energy for each array by summing the energy of k-$\omega$ pairs along the ray. Alternatively, other methods of accumulating energy along the ray (e.g., averaging) may be used. In any case, accumulated energy is determined for a range of trial velocities between a predetermined minimum velocity and a predetermined maximum velocity. The convective ridge 230 has an orientation that is the slope of the ray having the largest accumulated energy. The convective ridge identifier 232 provides information about the different trial convection velocities, information referred to generally as convective ridge information.

The analyzer 234 examines the convective ridge 230 information including the convective ridge 230 orientation (slope). Assuming the straight-line dispersion relation given by $k=\omega/u$, the analyzer 234 determines the flow velocity and/or volumetric flow, which are output as parameters 212. The volumetric flow is determined by multiplying the cross-sectional area of the inside of the pipe 104 with the velocity of the process flow 102. As previously noted, for turbulent, Newtonian fluids, there is typically not a significant amount of dispersion over a wide range of wavelength to diameter ratios. As a result, the convective ridge 230 in the k-$\omega$ plot is substantially straight over a wide frequency range and, accordingly, there is a wide frequency range for which the straight-line dispersion relation given by $k=\omega/u$ provides accurate flow velocity measurements.

For stratified flows, however, some degree of dispersion exists such that coherent structures 204 convect at velocities which depend on their size. As a result of increasing levels of dispersion, the convective ridge 230 in the k-$\omega$ plot becomes increasingly non-linear. For example, FIG. 14 depicts a k-$\omega$ plot having a non-linear ridge 230, which is shown having an exaggerated curvature for purposes of description. Thus, unlike the non-dispersive flows, determining the flow rate of a dispersive mixture by tracking the speed at which coherent structures 204 convect requires a methodology that accounts for the presence of significant dispersion. Referring to FIGS. 13, 14, and 15, a method 300 can be described for quantifying the level of stratification, as well as to measure the volumetric flow rate, in stratified flows. The method 300, generally indicated in FIG. 15, begins with block 302, where a velocity $U_1$ of the flow 102 is initialized. Initially, the velocity $U_1$ may be selected, for example, based on operating experience, expected velocities, and the like.

Next, in block 304, maximum and minimum frequencies ($F_{max}$ and $F_{min}$) defining a first frequency range $\Delta F_1$ are determined using the velocity $U_1$, the pipe diameter D, and maximum and minimum non-dimensional length scales FD/U. As will be discussed hereinafter, the maximum and minimum non-dimensional length scales may be determined using a calibration routine wherein the maximum and minimum non-dimensional length scales are selected to define a range centered on a non-dimensional length scale that is least sensitive to stratification. In the example shown in FIG. 14, a maximum non-dimensional length scale of FD/U=2.33 and a minimum non-dimensional length scale of FD/U=0.66 are used. Thus, for this example:

$$F_{max}=2.33*U_1/D, \text{ and}$$

$$F_{min}=0.66*U_1/D.$$

It will be appreciated, however, that different non-dimensional length scales may be used, depending on the results of the calibration routine.

The method 300 continues at block 306, where the convective ridge identifier 232 identifies the convective ridge 230 in the k-ω plot as a straight line 236 (FIG. 14) over the first frequency range $\Delta F_1$. In block 306, the convective ridge identifier 232 determines the slope of the straight line representation of the first convective ridge (e.g., the slope of line 236), and, using this slope, the analyzer 234 determines a nominal velocity $U_2$ (block 308). Recalling that FD/U is the inverse of λ/D, where λ is wavelength, the non-dimensional length scale of FD/U ranging from 0.66 to 2.33 corresponds to 1/D's (for λ=1) of 1.5 to 0.43. Note that the nominal velocity $U_2$ is centered on coherent structures with length scales of 0.667 diameters in length. After the nominal velocity $U_2$ is calculated over the frequency range $\Delta F_1$ in block 308, the nominal velocity $U_2$ is compared to the velocity $U_1$ in block 310 and, if the two velocities are equal (or approximately equal within an appropriate range), then the nominal velocity $U_2$ is provided as the nominal velocity U of the flow 102 (block 312), which may be used to determine volumetric flow rate of the flow 102.

If, however, the velocities $U_1$ and $U_2$ are not equal (or not within the appropriate range) in block 310, $U_1$ is set equal to $U_2$ (block 314) and the process returns to block 304 where the maximum and minimum frequencies ($F_{max}$ and $F_{min}$) defining the first frequency range $\Delta F_1$ are determined using the new velocity $U_1$. This iterative process continues until $U_1=U_2$ at block 310. After the nominal velocity U of the flow 102 is determined (block 312), average convection velocities are then calculated over a plurality of relatively small frequency ranges $\Delta F_2$. In method 300, this is accomplished by identifying a plurality of portions 238 (FIG. 14) of the convective ridge 230 over a plurality of second frequency ranges $\Delta F_2$ (block 316), where each second frequency range $\Delta F_2$ is smaller than the first frequency range $\Delta F_1$ and has a unique midpoint frequency, as shown at 240 in FIG. 14. The convective ridge identifier 232 then determines a slope of each portion 238 of the convective ridge 230 as a best fit line forced to fit through the origin and the portion of the convective ridge 230 (block 318).

Using the slope of each portion 238, the analyzer 234 determines a nominal convection velocity of coherent structures having a range of length scales corresponding to the associated second frequency range $\Delta F_2$ (block 320). Next, in block 322, the analyzer 234 normalizes these nominal convection velocities using the nominal velocity U, and then plots each normalized convection velocity as a function of the respective midpoint frequency 240 (non-dimensionalized by the nominal velocity U and the diameter D of the pipe) to create a dispersion plot (block 324). The functional dependency of the velocity versus frequency is captured by a linear fit (block 326). For non-dispersive flows, the linear fit would have a slope of 0.0 and a y-intercept of 1.0. Any variation to this can be attributed to dispersion. For flows with dispersion, the slope of the linear fit serves as a quantifiable measure of the stratification (block 328).

Figure 16:
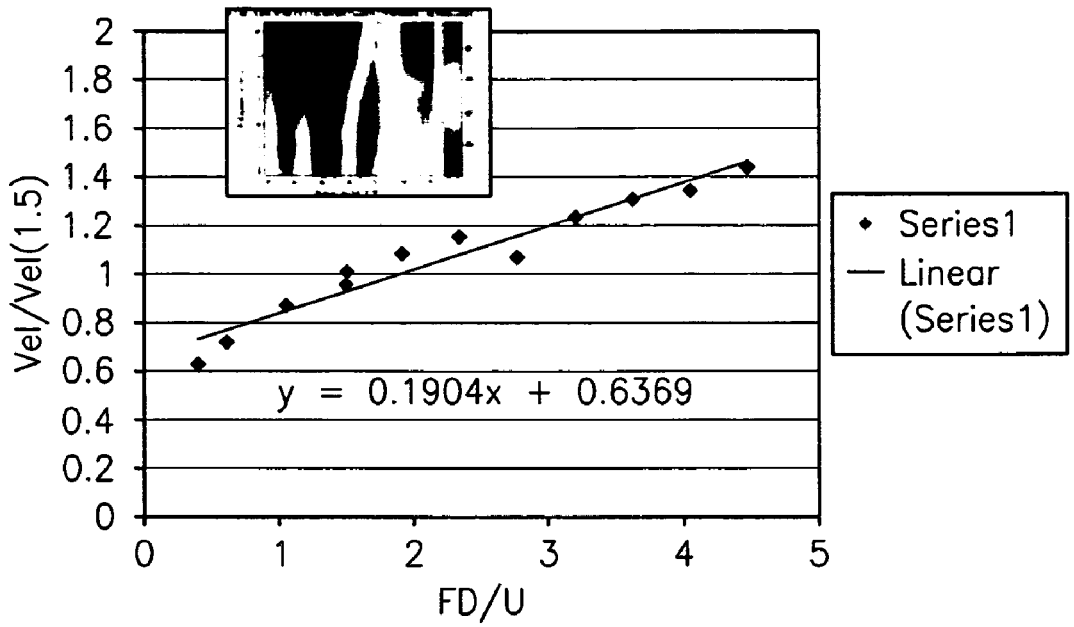
FIG. 16 depicts an example of a dispersion plot for a 30 inch hydrotransport line with a nominal velocity of 12 ft/sec created using the method of the present invention.

FIG. 16 depicts an example of a dispersion plot for a 30 inch hydrotransport line with a nominal velocity U of 12 ft/sec. created using the method of the present invention. For the example given in FIG. 16, the dispersion metric, i.e., the slope of the dispersion plot, is 19%, which indicates a significant amount of dispersion. The convection velocity, determined as described above for wavelengths of one diameter is 0.8 of the velocity of the wavelength with a length of 0.667 diameters (i.e., FD/U=1.5). Structures with wavelengths centered around ¼ diameters (i.e., FD/U=4) are shown to be convecting roughly 1.4 times the convection velocity of wavelengths centered around 0.667 diameters.

The dispersion plot can also be used as part of a calibration procedure to accurately determine the volumetric flow rate in the presence of stratification. For example, the range of non-dimensional length scales of FD/U used in determining the nominal flow velocity U may be selected as that range which is least sensitive to stratification. This may be accomplished, for example, by creating two or more dispersion plots, each at a different level of stratification. For example, in the hydrotransport of solids, dispersion plots may be created for different concentrations of solids. It has been determined that, as the slope of the linear fit of the dispersion plot increases from one level of stratification to another, the point about which the linear fit pivots provides a good approximation of the non-dimensional length scale FD/U that is least sensitive to stratification. Thus, the non-dimensional length scale FD/U that is least sensitive to stratification can be approximated by comparing the dispersion plots for different levels of stratification and identifying the pivot point of the linear fit of the dispersion plot from one dispersion plot to another. The non-dimensional length scale FD/U associated with the pivot point can be used as the mid-point for the range of non-dimensional length scales of FD/U used in method 300 of FIG. 15 for determining the nominal flow velocity U and the dispersion plot.

Figure 17:
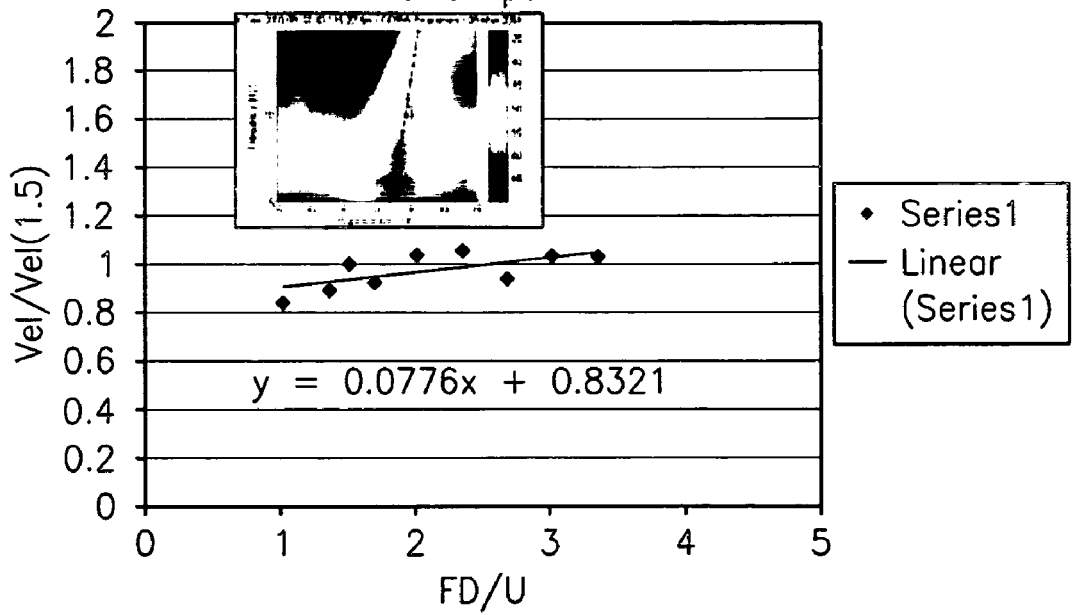
FIG. 17 depicts an example of a dispersion plot for a 27 inch hydrotransport line with a nominal velocity of 15 ft/sec created using the method of the present invention.
Figure 18:
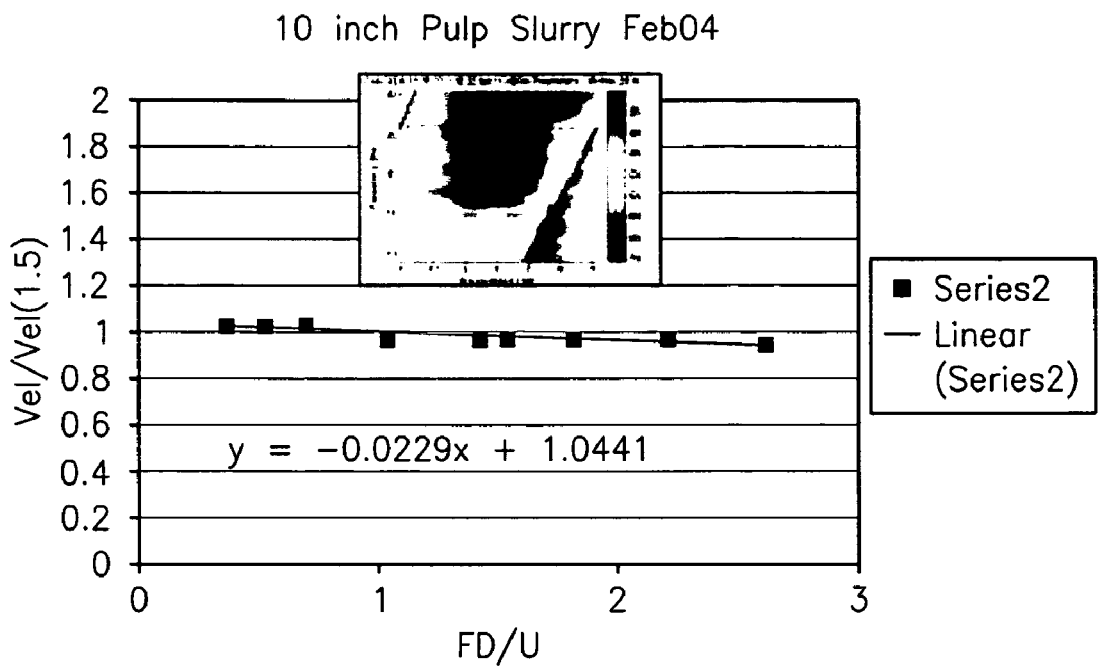
FIG. 18 depicts an example of a dispersion plot for a 10 inch, 1% consistency pulp-in-water suspension flowing at a nominal volumetric flow rate of 10 ft/sec created using the method of the present invention.
Figure 19:
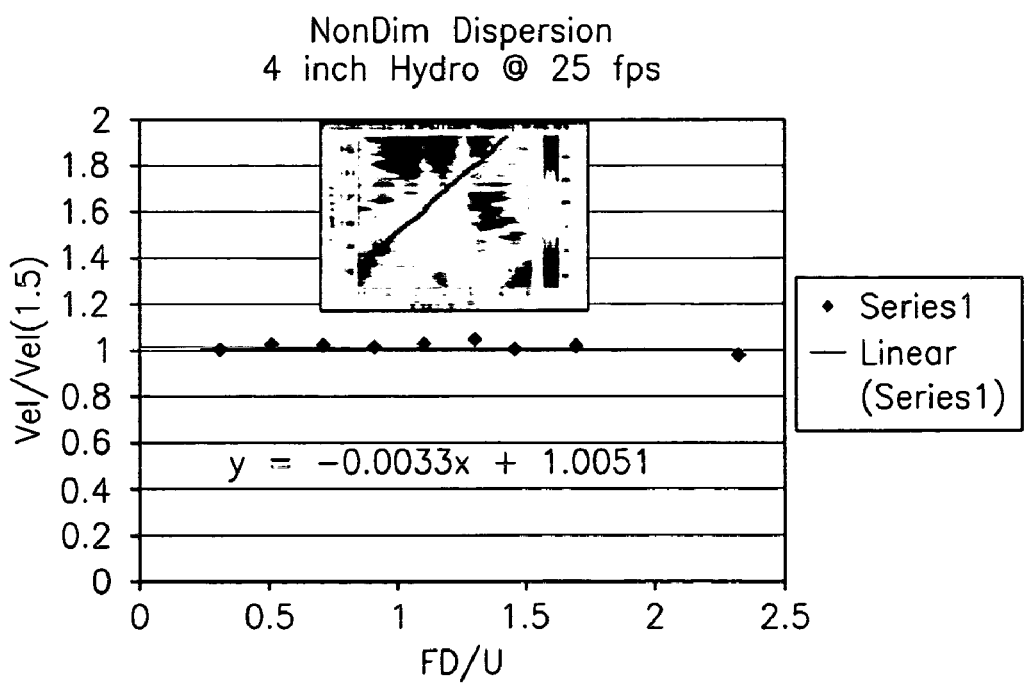
FIG. 19 depicts an example of a dispersion plot for a mixture of bitumen, sand, water, and air at 25 ft/sec in a 4 inch diameter pipe created using the method of the present invention.
Figure 20:
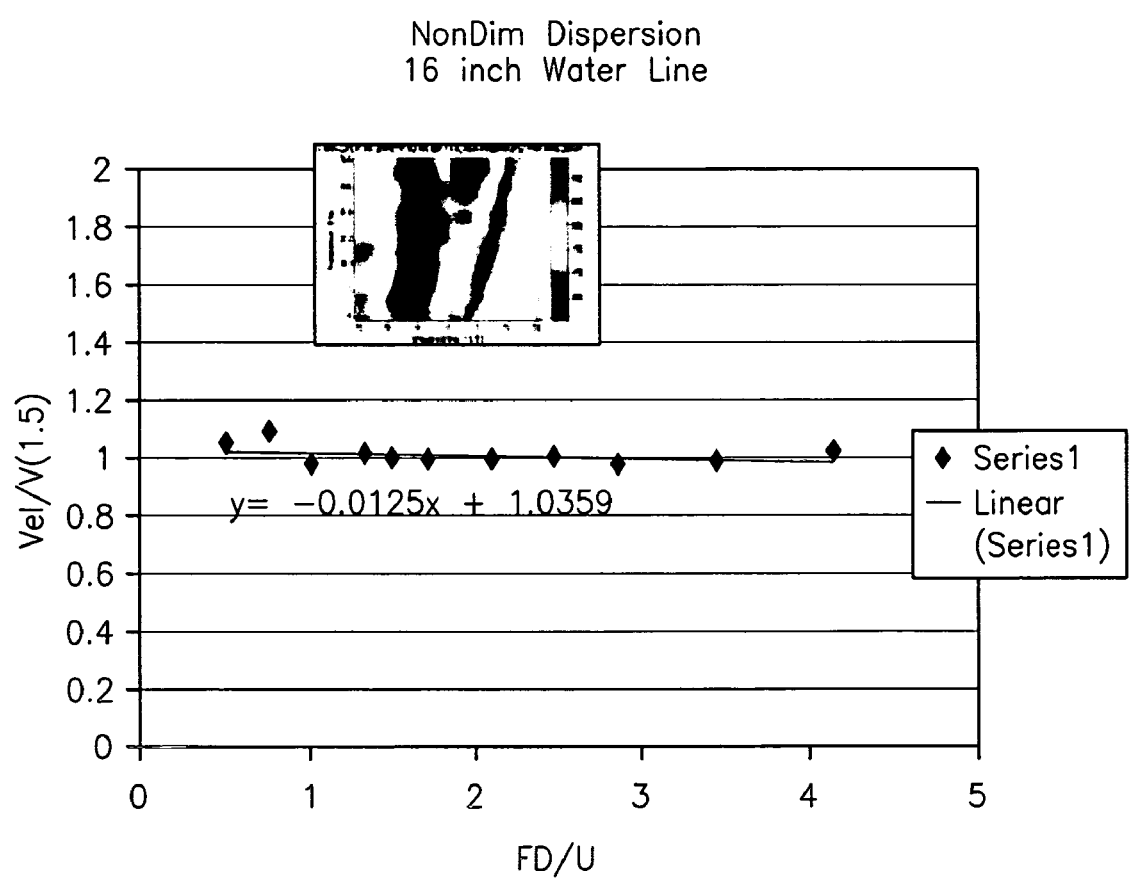
FIG. 20 depicts an example of a dispersion plot for a 16 inch pipe flowing water at a nominal flow velocity of 10 ft/sec created using the method of the present invention.

FIGS. 16-21 depict various examples of dispersion plots created using the method of the present invention. In each of these examples, a spatial wave number (i.e., FD/U) range of 0.66 to 2.33 with a center wave number of 1.5 was used. FIG. 17 shows an example of a hydrotransport of bitumen, sand, water, and air. In this case, the flow is in a 27 inch pipe, traveling at a nominal flow rate of 15 ft/sec. Here the slope of the dispersion plot is calculated to be 0.078 (i.e., a dispersion parameter of 7.8%). FIG. 18 shows a dispersion plot for a 10 inch, 1% consistency pulp-in-water suspension flowing at a nominal volumetric flow rate of 10 ft/sec. The resulting linear curve fit equation, shown in FIG. 18, has a slope of −0.023, which can be classified as non-dispersive flow. FIG. 19 shows a dispersion plot for a mixture of bitumen, sand, water, and air at 25 ft/sec in a 4 inch diameter pipe. The resulting linear curve fit equation, shown in FIG. 19, has a slope of −0.003, which can be classified as non-dispersive flow. FIG. 20 shows a dispersion plot for a 16 inch pipe flowing water at a nominal flow velocity of 10 ft/sec. The resulting linear curve fit equation, shown in FIG. 20, has a slope of −0.013, which can be classified as non-dispersive flow.

Figure 21:
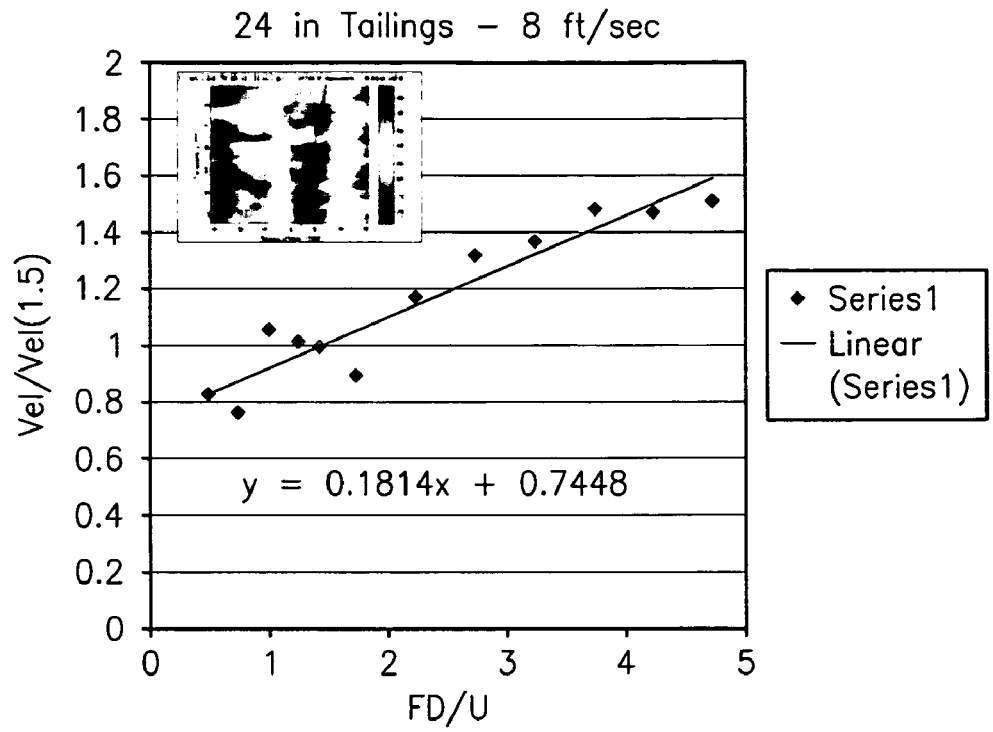
FIG. 21 depicts an example of a dispersion plot for a 24 inch tailings line operating at 8 ft/sec created using the method of the present invention.
Figure 22:
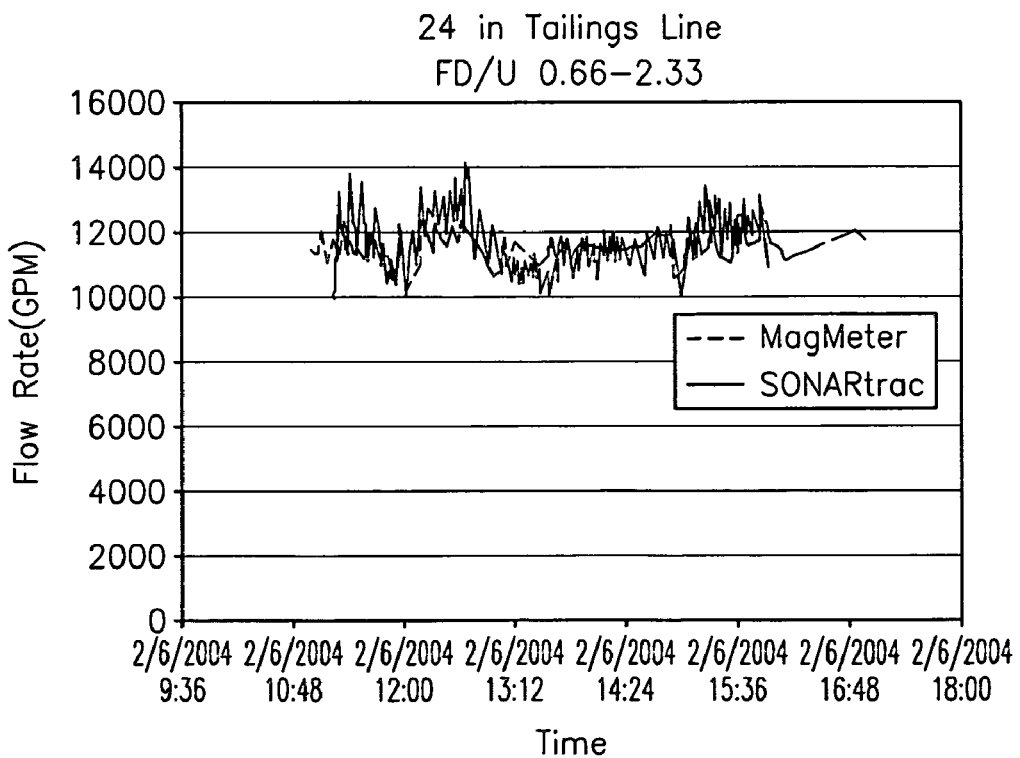
FIG. 22 is a plot depicting a flow rate determined by the method of the present invention demonstrated compared with a flow rate determined by an in-line magnetic flow meter.

FIG. 21 shows the dispersion characteristics for a 24 inch tailings line operating at 8 ft/sec. As shown, the tailings line is exhibiting a dispersion metric of about 18%. Using a spatial wave number (i.e. FD/U) range of 0.66 to 2.33 with a center wave number of 1.5, the velocity determined by the method of the present invention demonstrated good agreement with an in-line magnetic flow meter, as demonstrated in FIG. 22. Centering the frequency range on structure with a length scale of ⅔ the pipe diameter seems reasonable and consistent with conceptual model. Although accurate reference data from other stratified flows is currently not available, the similar dispersion characteristics suggest that using this, or similar, non-dimensional length scales should be a reasonable approach for interpreting the volumetric flow rates other stratified flows using sonar-based flow measurement.

Comparison of the examples provided in FIGS. 16-21 reveal that the slope of the dispersion curve tracks, at least qualitatively, is indicative of the level of stratification present. The slope approaches zero for well-mixed slurries and Newtonian fluids and increases with decreasing flow rates, consistent with stratification increasing with decreasing flow rates.

Figure 23:
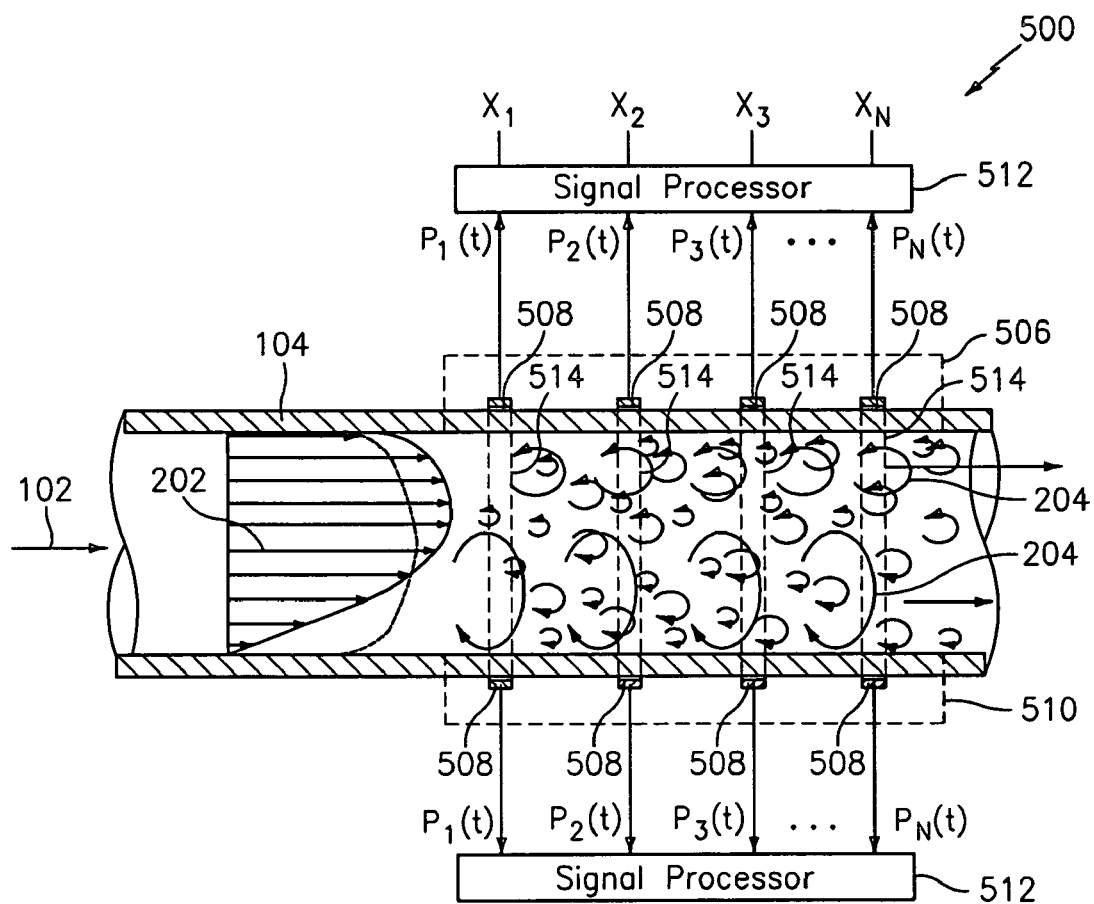
FIG. 23 depicts a longitudinal cross-section of an alternative embodiment of the present invention.
Figure 24:
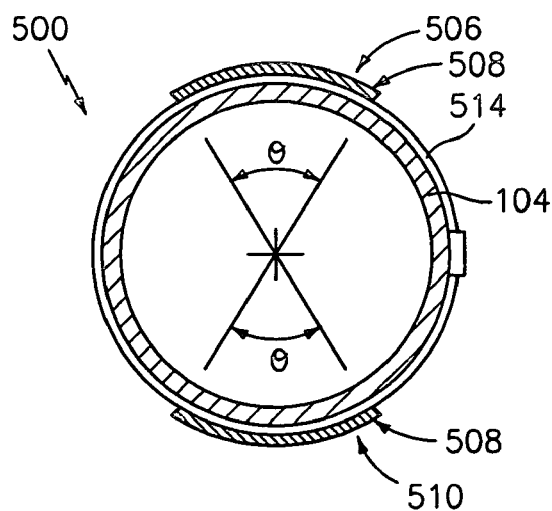
FIG. 24 depicts a transverse (radial) cross-section of the embodiment of FIG. 23.

FIG. 23 depicts a longitudinal cross-section of an apparatus 500 for determining the level of stratification of the flow 102 in accordance with an alternative embodiment of the present invention, and FIG. 24 depicts a transverse (radial) cross-section of the apparatus 500. It should be appreciated that once the level of stratification is know, the level of dispersion can be determined using the know relationships there between, as discussed in more detail hereinbefore. In this embodiment, the apparatus 500 determines the level of stratification of the flow 102 and a volumetric flow rate of the flow 102 by comparing locally measured velocities at the top and bottom of the pipe 104. The apparatus 500 includes a first spatial array 506 of at least two sensors 508 disposed at different axial locations $x_1 \ldots x_N$ along the top of the pipe 104. Each of the sensors 508 provides a pressure signal P(t) indicative of unsteady pressure created by coherent structures 204 convecting with a portion of the flow 102 near the top of the pipe 104. The apparatus 500 further includes a second spatial array 510 of at least two sensors 508 disposed at the different axial locations $x_1 \ldots x_N$ along the bottom of the pipe 104. Each of the sensors 508 in the second spatial array 510 provides a pressure signal P(t)' indicative of unsteady pressure created by coherent structures 204 convecting with a portion of the flow 102 near the bottom of the pipe 104.

The sensors 508 from each array 506 and 510 provide analog pressure time-varying signals $P_1(t), P_2(t), P_3(t) \ldots P_N(t)$ to one or more signal processors 512 to determine flow velocity of each array 506, 510. The signal processor 512 applies the pressure signals from the sensors 508 in the array 506 to flow logic 130 executed by the signal processor 512 to determine the velocity of the flow 102 near the top of the pipe 104. The signal processor 512 applies the pressure signals from the sensors 508 in the array 510 to flow logic 220 executed by the signal processor 512 to determine the velocity of the flow 102 near the bottom of the pipe 104. The flow logic 220 applies a sonar array-processing algorithm as described above with respect to FIGS. 12 and 13 to determine the velocities.

In the embodiment shown, each of the sensors 508 is formed by a strip of piezoelectric material such as, for example, the polymer, polarized fluoropolymer, PVDF, which measures the strain induced within the pipe 104 due to the coherent structures convecting with the flow 102. The sensors 508 can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The strips of piezoelectric film material forming the sensors 508 along each axial location $x_1 \ldots x_N$ of the pipe 104 may be adhered to the surface of a steel strap 514 (e.g., a hose clamp) that extends around and clamps onto the outer surface of the pipe 104. As discussed hereinafter, other types of sensors 508 and other methods of attaching the sensors 508 to the pipe 104 may be used.

In the embodiment shown, the sensors 508 extend over an arcuate outer surface of the pipe 104 defined by the angle θ, which is centered on a vertical line 516. For example, the each of the sensors 508 may extend about ¼ of the circumference of the pipe 104. Because the sensors 508 do not extend across the side surfaces of the pipe 104, and because the sensors 508 tend to sense local disturbances within the flow 102, the sensors 508 sense coherent structures 220 convecting with a portion of the flow 102 near the top or bottom of the pipe 104. Accordingly, as the size of the sensors 508 are decreased (i.e., as the angle θ is decreased), the unsteady pressures sensed by the sensors 508 more accurately indicate the nominal flow velocity of the portion of the flow 102 near the top or bottom of the pipe 104. However, the degree of accuracy provided by decreasing the size of the sensors 508 is offset by the decrease in signal strength provided by the sensors 508. Therefore, the size of the sensors 508 (i.e., the angle θ used) is dependent at least on the degree of accuracy desired and the strength of the signals $P_1(t), P_2(t), P_3(t) \ldots P_N(t)$ required by the signal processor 512.

While the apparatus 500 is shown as including four sensors 508 in each array 506 and 510, it is contemplated that each array 506 and 510 may include two or more sensors 508, with each sensor 508 providing a pressure signal P(t) indicative of unsteady pressure within the pipe 104 at a corresponding axial location X of the pipe 104. For example, the apparatus 500 may include 2, 3, 4, 5, 6, 7, 8, 9, 10, 11, 12, 13, 14, 15, 16, 17, 18, 19, 20, 21, 22, 23, or 24 sensors 508. Generally, the accuracy of the measurement improves as the number of sensors 508 in the arrays 506 and 510 increases. The degree of accuracy provided by the greater number of sensors 508 is offset by the increase in complexity and time for computing the desired output parameter of the flow 102. Therefore, the number of sensors 508 used is dependent at least on the degree of accuracy desired and the desire update rate of the output parameter provided by the apparatus 500.

Figure 25:
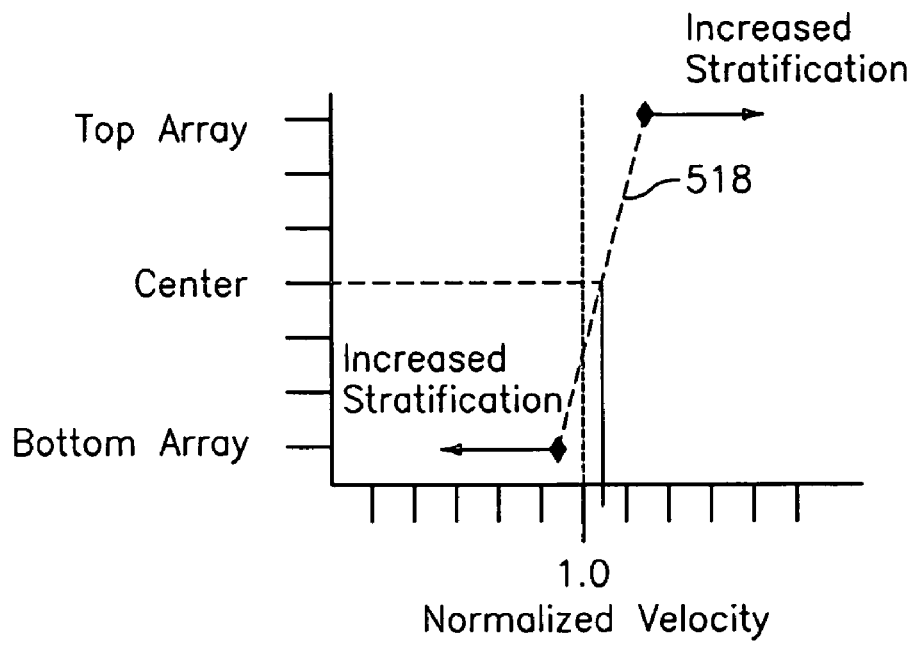
FIG. 25 depicts a plot of the normalized velocity for the top and bottom arrays in the embodiment of FIG. 23.

FIG. 25 depicts a plot of the normalized velocity for the top and bottom arrays 506 and 510. The ratio of the velocities near the top and bottom of the pipe 104 correlates to the level of stratification of the flow 102. Under conditions where there is no stratification, flow 102 near the top and bottom of the pipe 104 (and the coherent structures 220 convecting with the flow 102) will travel at approximately the same velocity. As the level of stratification increases, the top array 506 will measure a higher normalized velocity and the bottom array 510 will measure a lower normalized velocity. Thus, by comparing the velocities near the top and bottom of the pipe 104, the level of stratification of the flow 102 can be determined.

The velocities near the top and bottom of the pipe 104 can also be used to estimate the nominal velocity of the flow 102, which, in turn, may be used to determine the volumetric flow rate of the flow 102. For example, nominal velocity may be determined using an average of the two velocities or some other ratio of the two velocities, wherein the ratio is dependent on the level of stratification (or difference between the two velocities). In another example, as shown in FIG. 25, the velocities near the top and bottom of the pipe 104 may be plotted as a function of the distance between the top and bottom arrays 506, 510. In this example, the distance between the top and bottom arrays 506, 510 is approximately equal to the pipe diameter, and each increment on the x-axis represents some portion of this distance. The velocities at the top and bottom of the pipe 104 define a straight line 518, which has a slope that changes with the level of stratification. Using this straight line 518, the velocities at different distances between the top and bottom of the pipe 104 can be estimated, and the velocity at the appropriate pipe location can be used as the nominal velocity. In the example shown, velocity at the center of the pipe 104 (mid-way between the top 506 and bottom 510 arrays) is estimated.

Figure 26:
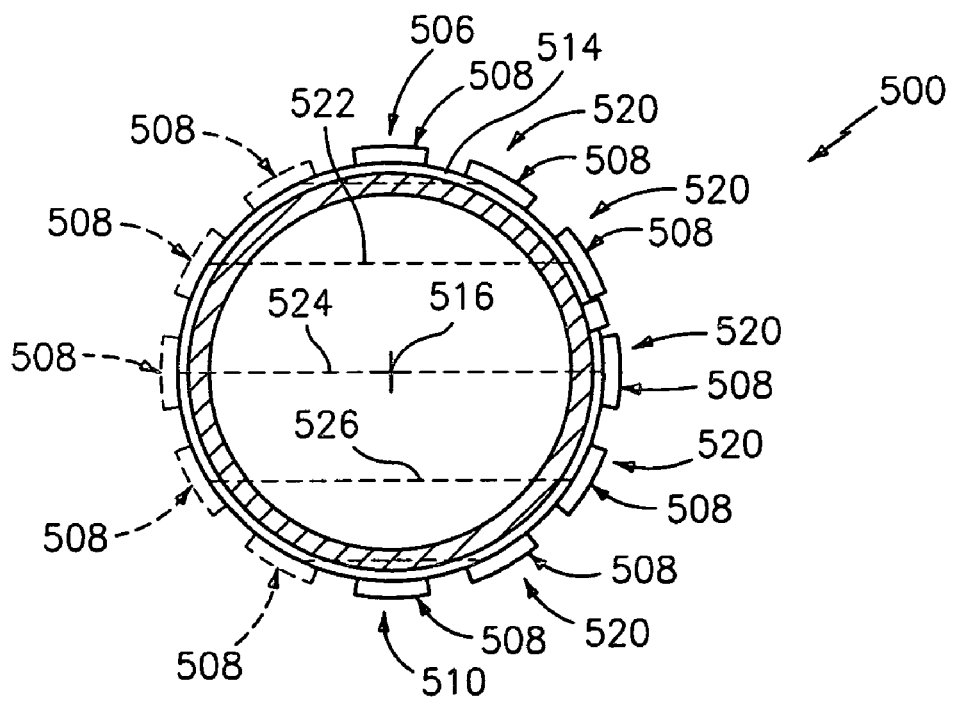
FIG. 26 depicts a transverse (radial) cross-section of the embodiment of FIG. 23 including additional arrays of sensors.
Figure 27:
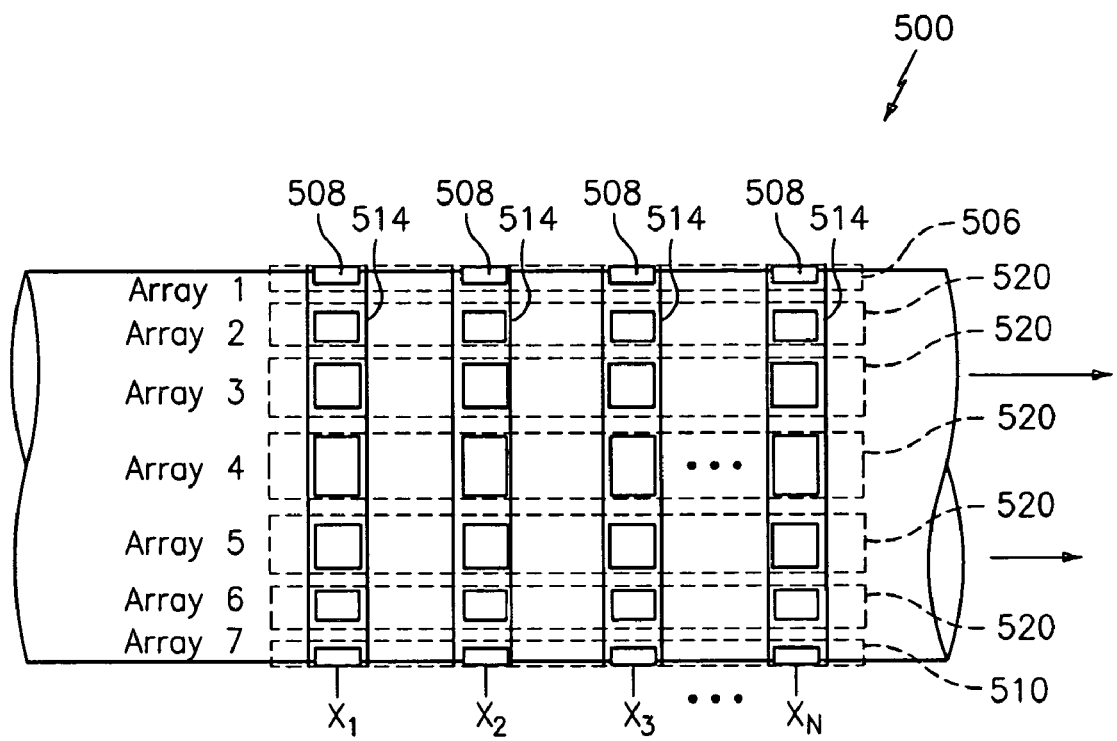
FIG. 27 depicts a side elevation view of the embodiment of FIG. 23 including additional arrays of sensors.

FIG. 26 depicts a transverse (radial) cross-section of the apparatus 500 of FIG. 24, further including at least one additional spatial array 520 of sensors 508 aligned axially along the pipe 104 and being positioned between the first and second spatial arrays 506 and 510. FIG. 27 depicts a side elevation view of this embodiment. The sensors 508 in each additional array 520 provide analog pressure time-varying signals $P_1(t)$, $P_2(t)$, $P_3(t)$ ... $P_N(t)$ to one or more signal processors 512, which determines flow velocity of the fluid 102 proximate each additional array 520. Optionally, each array 520 may comprise a pair of sensors 508 disposed on the pipe 104 at a corresponding level between the top and bottom arrays 506 and 510, as indicated at 522, 524, and 526. These optional sensors 508 are shown in phantom in FIG. 26. For each array, the signal output from the pair of sensors 508 at corresponding axial locations $x_1$ ... $x_N$ are combined (e.g., summed) as a single input to the signal processor 512 to eliminate portions of the signal caused by horizontal bending modes of the pipe 104.

Figure 28:
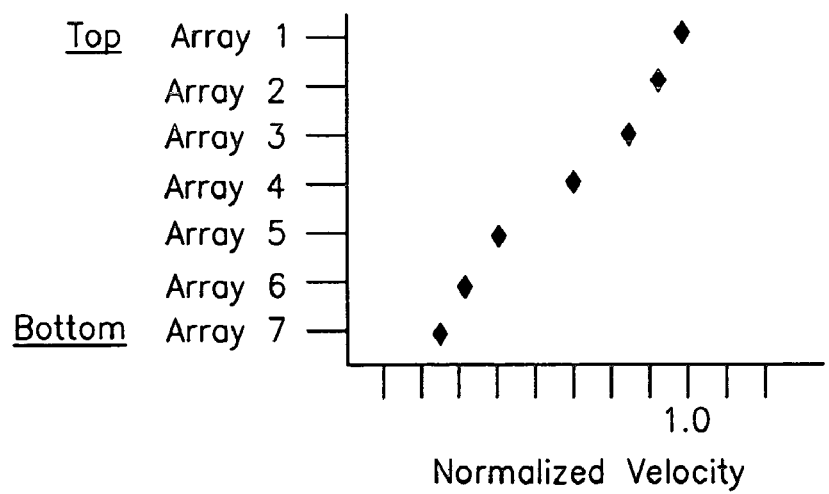
FIG. 28 depicts a plot of normalized velocity sensed by each array of FIGS. 26 and 28.

FIG. 28 depicts a plot of the normalized velocity for each array 506, 510, and 520. As in the example of FIG. 25, the ratio of the velocities near the top and bottom of the pipe 104 correlates to the level of stratification of the flow 102. The additional arrays 520 allow a velocity profile to be constructed, with the number of data points in the profile being equal to the number of arrays 506, 510 and 520. Comparing the velocity profiles of FIG. 25 and FIG. 28, it can be seen that the additional arrays 520 used to create the profile of FIG. 28 allow for a more accurate representation of the velocities at different locations in the pipe 104 than the straight line approximation of FIG. 25.

As can be seen in the velocity profile of FIG. 28, the extreme top and bottom velocity readings (i.e. the velocity readings at Arrays 1 and 7 in FIG. 27, respectively) tend to be the most diverse, with the reading at the transverse sides of the pipe 104 (i.e. the reading at Array 4 in FIG. 27) providing a nominal velocity for the entire profile. Accordingly, it can be seen that for measuring nominal velocity in stratified flow using an array of sensors 508, it may be advantageous to sense unsteady pressures along the transverse sides of the pipe 104, such that the areas of extreme diversity in velocity (i.e., the top and bottom of the pipe 104) are ignored. For example, the center-most array (Array 4 in FIG. 27) may be used to determine the nominal velocity of the flow 102, or the center-most arrays (e.g., arrays 3, 4, and 5 in FIG. 27) can be used to determine the nominal velocity of the flow 102. The present invention also contemplates that any array offset from the center horizontal array (i.e. Array 4 in FIG. 27), such as Arrays 4 and Array 5 in FIG. 27 or combinations of other arrays (e.g. Arrays 2 & 3 or Arrays 5 & 6 in FIG. 27) may be used to determine the nominal or average velocity of the process flow 102. The determination of which array or set of arrays to determine the nominal velocity is dependent on the level of stratification.

In any of the embodiments described herein, the sensors may include electrical strain gages, optical fibers and/or gratings, ported sensors, ultrasonic sensors, among others as described herein, and may be attached to the pipe by adhesive, glue, epoxy, tape or other suitable attachment means to ensure suitable contact between the sensor and the pipe 104. The sensors may alternatively be removable or permanently attached via known mechanical techniques such as mechanical fastener, spring loaded, clamped, clam shell arrangement, strapping or other equivalents. Alternatively, strain gages, including optical fibers and/or gratings, may be embedded in a composite pipe 104. If desired, for certain applications, gratings may be detached from (or strain or acoustically isolated from) the pipe 104 if desired. It is also contemplated that any other strain sensing technique may be used to measure the variations in strain in the pipe 104, such as highly sensitive piezoelectric, electronic or electric, strain gages attached to or embedded in the pipe 104.

In various embodiments of the present invention, a piezoelectronic pressure transducer may be used as one or more of the pressure sensors and it may measure the unsteady (or dynamic or ac) pressure variations inside the pipe 104 by measuring the pressure levels inside the pipe 104. In one embodiment of the present invention, the sensors comprise pressure sensors manufactured by PCB Piezotronics of Depew, N.Y. For example, in one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The sensors may incorporate a built-in MOSFET microelectronic amplifier to convert the high-impedance charge output into a low-impedance voltage signal. The sensors may be powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Furthermore it is contemplated that each of the sensors 604 may include a piezoelectric sensor that provides a piezoelectric material to measure the unsteady pressures of the flow 102. The piezoelectric material, such as the polymer, polarized fluoropolymer, PVDF, measures the strain induced within the process pipe 104 due to unsteady pressure variations within the flow 102. Strain within the pipe 104 is transduced to an output voltage or current by the attached piezoelectric sensors 604.

The PVDF material forming each piezoelectric sensor may be adhered to the outer surface of a steel strap that extends around and clamps onto the outer surface of the pipe 104. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique include the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals.
5. Higher Temperatures (140C) (co-polymers)

It should be appreciated that the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

It should be understood that any of the features, characteristics, alternatives or modifications described regarding a particular embodiment herein may also be applied, used, or incorporated with any other embodiment described herein. In addition, it is contemplated that, while the embodiments described herein are useful for flow having dispersive properties (e.g., stratified flow), the embodiments described herein can also be used for homogeneous flow with no dispersive properties. Although the invention has been described and illustrated with respect to exemplary embodiments thereof, the foregoing and various other additions and omissions may be made therein and thereto without departing from the spirit and scope of the present invention.

What is claimed is:

1. An industrial meter for measuring the size and distribution of particles within a fluid flowing within a pipe, the industrial meter comprising:
    at least one metering device configured to respond to a mixture density, an average flow rate and a dispersion of the fluid flowing within the pipe and provide at least one metering device signal containing information about the same; and
    a processing device configured to respond to the at least one signal and provide a processor device signal containing information about the size and distribution of particles within the fluid flowing within the pipe that depends on the mixture density, the average flow rate and the dispersion of the fluid flowing within the pipe.

2. The industrial meter of claim 1, wherein said density meter includes at least one of a Coriolis meter and a nuclear densitometer.

3. The industrial meter of claim 1, wherein said velocity meter includes at least one of a magmeter, a sonar flow meter and a venture meter.

4. The industrial meter of claim 1, wherein said dispersion meter includes at least two sensing device associated with the pipe to measure the flow velocity in at least two locations within the pipe.

5. The industrial meter of claim 1, wherein said at least one metering device includes a plurality of sensors disposed external to the pipe.

6. The industrial meter of claim 1, wherein said dispersion meter includes a first sensing device and a second sensing device, said first sensing device being disposed to sense a fluid characteristic at a first location in the pipe and said second sensing device being disposed to sense a fluid characteristic at a second location in the pipe.

7. The industrial meter of claim 6, wherein said first location is at least one of a top pipe portion and a middle pipe portion and wherein said second location is at least one of a bottom pipe portion and said middle pipe portion.

8. The industrial meter of claim 6, wherein said fluid characteristic includes at least one of said mixture density of the fluid, said flow rate of the fluid and said dispersion of the fluid.

9. The industrial meter of claim 1, wherein said processing device further includes a means for generating said fluid information responsive to a dispersion metric, wherein the dispersion metric is expressed as the slope of a line of best fit of a dispersion plot.

10. An industrial meter according to claim 1, wherein the processor device determines the particle size or distribution based on a particle size metric and an empirical calibration approach, including where an increasing particle size metric correlates to an increasing particle size.

11. An industrial meter according to claim 10, wherein the processor device determines the particle size metric based on the equation, as follows:

$$\Gamma = f(\Delta, \rho_{mix}, V),$$

wherein $\Delta$ is the dispersion metric, $\rho_{mix}$ is the mixture specific gravity and V is the average mixture velocity in ft/sec.

12. An industrial meter according to claim 1, wherein the dispersion contains information about the dependence of convection velocity with wavelength, or equivalently with temporal frequency.

13. An industrial meter for measuring the size and distribution of particles within a fluid flowing within a pipe, the industrial meter comprising:
    at least one metering device for determining at least one of the mixture density of the fluid, the flow rate of the fluid and the dispersion of the fluid,
    wherein said at least one metering device generates meter data responsive to at least one of said mixture density of the fluid, said flow rate of the fluid and said dispersion of the fluid, and
    wherein said at least one metering device includes at least one of a density meter, a velocity meter and a dispersion meter; and
    a processing device communicated with said at least one metering device, wherein said processing device receives and processes said meter data to generate fluid information corresponding to a dispersive mixture of the fluid, the fluid information including a particle size metric responsive to a dispersion metric, specific gravity and average velocity of the dispersive mixture, and wherein the processing device provides output corresponding to a size and distribution of the particles within the fluid;

wherein said processing device includes a means for generating said fluid information responsive to the particle size metric, wherein the particle size metric is expressed as, $\Gamma = f(\Delta, \rho_{mix}, V)$, wherein $\Delta$ is the dispersion metric, $\rho_{mix}$ is the mixture specific gravity and V is the average mixture velocity.

14. A method for measuring the size and distribution of particles within a multiphase fluid flowing within a pipe, the method comprising:

receiving flow data responsive to at least one fluid characteristic of a dispersive mixture of the fluid flowing with the pipe;

using a processing device for identifying a particle size metric responsive to said at least one fluid characteristic, said at least one fluid characteristic including at least one of a dispersion metric, a specific gravity and an average velocity of the dispersive mixture, said particle size metric being defined as, $\Gamma = f(\Delta, (\rho_{mix} - 1)^m, V^n)$, wherein $\Delta$ is the dispersion metric, $\rho_{mix}$ is the mixture specific gravity and V is the average mixture velocity in ft/sec; and providing an output corresponding to at least one of a particle size and a particle distribution of the particles within the dispersive mixture of the fluid.

15. The method of claim 14, wherein said dispersion metric is determined by, selecting an initial velocity of the fluid flowing within the pipe;

responsive to said initial velocity, determining a first frequency range within the fluid;

identifying a convective ridge within the fluid for said first frequency range;

calculating a nominal velocity of the fluid for said first frequency range;

dividing said first frequency range into a plurality of second frequency ranges;

determining an average convection velocity for each of said plurality of second frequency ranges;

for each of said plurality of second frequency ranges, determining a nominal convection velocity of coherent structures having a range of length scales corresponding to said second frequency range;

for each of said plurality of second frequency ranges, normalizing said nominal convection velocity; and providing a level of dispersion for the fluid.

16. The method of claim 15, wherein said first frequency range is defined by a maximum frequency and a minimum frequency, wherein said maximum frequency and said minimum frequency are responsive to said initial velocity, the diameter of the pipe and a predetermined non-dimensional length scale and wherein said predetermined non-dimensional length scale includes a minimum non-dimensional length scale value and a maximum non-dimensional length scale value.

17. The method of claim 15, further comprising comparing said initial velocity and said nominal velocity to determine if said initial velocity is equal to said nominal velocity.

18. The method of claim 15, wherein said determining a nominal velocity of coherent structures includes determining a slope for each of said plurality of sub-frequency ranges.

19. The method of claim 15, wherein said determining a level of dispersion includes, plotting said normalized convection velocity as a function of their respective non-dimensionalized mid-point frequency to create a dispersion plot;

determining a best-fit linear function for said plot; and determining level of dispersion using slope of said best-fit linear function.

20. The method of claim 14, further comprising determining a stratification of the fluid flow and empirically determining the dispersion of the fluid flow responsive to said stratification of the fluid flow.

21. A method for measuring the size and distribution of particles within a multiphase fluid flowing within a pipe, the method comprising:

responding with at least one metering device to a mixture density, an average flow rate and a dispersion of the fluid flowing within the pipe, and providing at least one metering device signal containing information about the same; and responding with a processing device to the at least one signal, and providing a processor device signal containing information about the size and distribution of particles within the fluid flowing within the pipe that depends on the mixture density, the average flow rate and the dispersion of the fluid flowing within the pipe.

22. A method according to claim 21, wherein the method comprises determining in the processor device the particle size or distribution based on a particle size metric and an empirical calibration approach, including where an increasing particle size metric correlates to an increasing particle size.

23. A method according to claim 22, wherein the method comprises determining in the processor device the particle size metric based on the equation, as follows:

$\Gamma = f(\Delta, \rho_{mix}, V)$, wherein $\Delta$ is the dispersion metric, $\rho_{mix}$ is the mixture specific gravity and V is the average mixture velocity in ft/sec.

24. A method according to claim 21, wherein the dispersion contains information about the dependence of convection velocity with wavelength, or equivalently with temporal frequency.

25. A system for determining characteristics and efficiency related to the processing of a multiphase fluid flowing in a pipe, comprising:

two monitoring devices, each being arranged at a separate point on the pipe, and each having an industrial meter configured for measuring the size and distribution of particles within the multiphase fluid flowing within the pipe, and comprising at least one metering device configured to respond to a mixture density, an average flow rate and a dispersion of the fluid flowing within the pipe and provide at least one metering device signal containing information about the same, and a processor device configured to respond to the at least one signal and provide a processor device signal containing information about a particle size metric containing information about the size and distribution of particles within the fluid flowing within the pipe that depends on the mixture density, the average flow rate and the dispersion of the fluid flowing within the pipe; and a system processor device configured to respond to the processor device signal, compare the particle size or distribution at each location, and provide a system processor signal indicative of the efficiency or amount of reduction in the size of the particles of the multiphase fluid flowing in the pipe.

26. A system according to claim 25, wherein the system is adjusted based on a difference between the particle size or distribution at the different locations.

27. A system according to claim 25, wherein the processor device determines the particle size or distribution based on a particle size metric and an empirical calibration approach, including where an increasing particle size metric correlates to an increasing particle size.

28. A system according to claim 27, wherein the processor device determines the particle size metric based on the equation, as follows:

$$\Gamma = f(\Delta, \rho_{mix}, V),$$

wherein $\Delta$ is the dispersion metric, $\rho_{mix}$ is the mixture specific gravity and V is the average mixture velocity in ft/sec.

* * * * *